(12) United States Patent
Cheng et al.

(10) Patent No.: US 12,365,665 B2
(45) Date of Patent: Jul. 22, 2025

(54) SOLID FORM OF DIAMINOPYRIMIDINE COMPOUND OR HYDRATE THEREOF, PREPARATION METHOD THEREFOR, AND APPLICATION THEREOF

(71) Applicant: BEIJING TIDE PHARMACEUTICAL CO., LTD., Beijing (CN)

(72) Inventors: CheungLing Cheng, Beijing (CN); Yanping Zhao, Beijing (CN); Hongjun Wang, Beijing (CN); Zewang Feng, Beijing (CN); Huai Huang, Beijing (CN); Kai Liu, Beijing (CN); Xuelian Liu, Beijing (CN); Jianmei Pang, Beijing (CN); Nana Tian, Beijing (CN); Xichao Chen, Beijing (CN); Shenzhen Fu, Beijing (CN); Jie Meng, Beijing (CN); Liying Zhou, Beijing (CN); Yanan Liu, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 763 days.

(21) Appl. No.: 17/607,449

(22) PCT Filed: Apr. 29, 2020

(86) PCT No.: PCT/CN2020/087687
§ 371 (c)(1),
(2) Date: Oct. 29, 2021

(87) PCT Pub. No.: WO2020/221275
PCT Pub. Date: Nov. 5, 2020

(65) Prior Publication Data
US 2022/0204475 A1    Jun. 30, 2022

(51) Int. Cl.
C07D 401/12    (2006.01)

(52) U.S. Cl.
CPC ........ C07D 401/12 (2013.01); C07B 2200/13 (2013.01)

(58) Field of Classification Search
None
See application file for complete search history.

(56) References Cited

U.S. PATENT DOCUMENTS 10,457,740 B1    10/2019    Kahvejian et al.
11,414,444 B2 *   8/2022    Zhao .................... C07F 9/5325
(Continued)

FOREIGN PATENT DOCUMENTS

CA    3041420    6/2018
CA    3076680    5/2019
(Continued)

OTHER PUBLICATIONS

Atipamula et al., Cryst. Growth Des. 2012, 12, 5, 2147-2152 (Year: 2012).*

(Continued)

*Primary Examiner* — Jeffrey S Lundgren
*Assistant Examiner* — Anthony Joseph Seitz
(74) *Attorney, Agent, or Firm* — Robin L. Teskin; Baker, Donelson, Bearman, Caldwell & Berkowitz PC

(57) ABSTRACT

The present invention relates to a solid form of 5-((2-ethynyl-5-isopropylpyridin-4-yl)oxy)pyrimidine-2,4-diamine or a hydrate thereof, a method for preparing the solid form, a pharmaceutical composition comprising the solid form, and a use of the solid form for the prevention or treatment of a disease modulated by P2X3 and/or P2X2/3 receptor antagonists.

25 Claims, 11 Drawing Sheets

(56) References Cited

U.S. PATENT DOCUMENTS

| | | |
|---|---|---|
| 2007/0049758 A1 | 3/2007 | Dillon et al. |
| 2019/0389811 A1 | 12/2019 | Hawley et al. |
| 2020/0239421 A1 | 7/2020 | Hawley et al. |
| 2021/0009531 A1 | 1/2021 | Broka et al. |
| 2022/0389039 A1 | 12/2022 | Zhao et al. |

FOREIGN PATENT DOCUMENTS

| | | |
|---|---|---|
| CN | 1930135 | 3/2007 |
| CN | 101296907 | 10/2008 |
| CN | 102070614 | 5/2011 |
| CN | 108778280 | 11/2018 |
| CN | 108778282 | 11/2018 |
| CN | 108779119 | 11/2018 |
| CN | 108834412 | 11/2018 |
| EA | 014706 B1 | 2/2011 |
| EP | 3964500 | 3/2022 |
| JP | 2007526268 | 9/2007 |
| JP | 2009513565 | 4/2009 |
| JP | 2018203648 | 12/2018 |
| JP | 2019508445 | 3/2019 |
| JP | 2019510025 | 4/2019 |
| JP | 2021501184 | 1/2021 |
| MX | 2018011136 | 1/2019 |
| WO | 2006127926 | 11/2006 |
| WO | 2017160569 | 9/2017 |
| WO | 2017165255 | 9/2017 |
| WO | 2019085916 | 5/2019 |

OTHER PUBLICATIONS

Ford AP. In pursuit of P2X3 antagonists: novel therapeutics for chronic pain and afferent sensitization. Purinergic Signalling. Feb. 2012;8(Suppl 1):3-26.

Jarvis MF, Burgard EC, McGaraughty S, Honore P, Lynch K, Brennan TJ, Subieta A, Van Biesen T, Cartmell J, Bianchi B, Niforatos W. A-317491, a novel potent and selective non-nucleotide antagonist of P2X3 and P2X2/3 receptors, reduces chronic inflammatory and neuropathic pain in the rat. Proceedings of the National Academy of Sciences. Dec. 24, 2002;99(26):17179-84.

McGaraughty S, Wismer CT, Zhu CZ, Mikusa J, Honore P, Chu KL, Lee CH, Faltynek CR, Jarvis MF. Effects of A-317491, a novel and selective P2X3/P2X2/3 receptor antagonist, on neuropathic, inflammatory and chemogenic nociception following intrathecal and intraplantar administration. British journal of pharmacology. Dec. 2003;140 (8):1381-8.

Kaan TK, Yip PK, Patel S, Davies M, Marchand F, Cockayne DA, Nunn PA, Dickenson AH, Ford AP, Zhong Y, Malcangio M. Systemic blockade of P2X3 and P2X2/3 receptors attenuates bone cancer pain behaviour in rats. Brain. Sep. 1, 2010;133(9):2549-64.

Caira M R: "Crystalline Polymorphism of Organic Compounds", Topics in Current Chemistry, Springer, Berlin, DE, vol. 198, Jan. 1, 1998 (Jan. 1, 1998), pp. 163-208.

Kuznecova G. A. "Metodičeskie ukazaniâ" ["Methodical guidelines"], Irkutsk State University, Chair for General Physics, 2005, p. 3 par. 2.

Pinto M. A. L. et al., Thermoanalytical studies of carbamazepine: hydration/dehydration, thermal decomposition, and solid phase transitions. Brazilian Journal of Pharmaceutical Sciences, 2014, vol. 50, pp. 877-884 (abstract)).

Bernstein J. "Polimorfizm molekulârnyh kristallov" ["Polymorphism in Molecular Crystals"], Moscow: Nauka, 2007, Chapter 7.3.2. Bioavailability pp. 324-330.

C. Reichardt "Rastvoriteli i effekty sredy v organičeskoj himii [Solvents and Solvent Effects in Organic Chemistry]", Mir, 1991, 763 pages (pp. 611-614, Section A5).

Barbara Rodriguez-Spong et al.: 'General principles of pharmaceutical solid polymorphism: a supramolecular perspective Advanced Drug Delivery Reviews, 2004, 56, pp. 241-274 (pp. 262-263).

K. Kummerer, Pharmaceuticals in the environment, Annual Review of Environment and Resources, 2010, v.35, pp. 57-75, doi: 10.1146/annurev-environ-052809-161223 (see abstract, p. 60)).

Mino. R. Caira, Crystalline polymorphism of organic compounds, Topics in Current Chemistry, Springer Verlag Berlin Heidelberg, 1998, vol. 198, pp. 163-208, namely pp. 164-166, Section 3.1.

Narayan Variankav et al. "From form to function: Crystallization of active pharmaceutical ingredients", AIChE, 2008, vol. 54(7), pp. 1682-1688 (p. 1682 "Crystal Form"; doi:10.1002/aic. 11555).

Stephen Byrn et al.: Pharmaceutical Solids: A Strategic Approach to Regulatory Considerations, Review, Pharmaceutical Research, 1995, vol. 12, No. 7, p. 945-954 "Hydrate (Solvate)".

Fang Tian et al. "Factors affecting crystallization of hydrates". Journal of Pharmacy and Pharmacology, 2010, vol. 62, pp. 1534-1546 (pp. 1534 Introduction, pp. 1535-1536 (right column, second paragraph) (doi.10.1111/j.2042-7158.2010.01186.x).

Hilfiker R. "Polymorphism in the Pharmaceutical Industry", WILEY-VCH, 2006, 425 p. (p. 10 paragraph 2).

Zefirova O. N. et al. "Ob istorii vozniknoveniâ i razvitiâ koncepcii bioizosterizma" ["On the history of the emergence and development of the concept of bioisosterism"], Bulletin of Moscow University, Himiâ, 2002, vol. 43, 4, pp. 251-256.

Russian Office Action for Russian Pat. Appl. No. 2021 134 261, dated Mar. 18, 2024, with the English translation and Search Report (32 total pages),.

\* cited by examiner

SOLID FORM OF DIAMINOPYRIMIDINE COMPOUND OR HYDRATE THEREOF, PREPARATION METHOD THEREFOR, AND APPLICATION THEREOF

CROSS-REFERENCE TO RELATED APPLICATIONS

This application is a U.S. National Phase application of Int'l Appl. No. PCT/CN2020/087687, filed Apr. 29, 2020, which claims priority to Int'l Appl. No. PCT/CN2019/085207, filed Apr. 30, 2019, each of which are incorporated herein by reference in their entireties.

FIELD OF THE INVENTION

The present invention relates to a solid form of 5-((2-ethynyl-5-isopropylpyridin-4-yl)oxy)pyrimidine-2,4-diamine (hereinafter referred to as "compound A") or a hydrate thereof, a method for preparing the solid form, a pharmaceutical composition comprising the solid form, and a use of the solid form for the prophylaxis or treatment of a disease mediated by a P2X3 and/or P2X2/3 receptor antagonist.

BACKGROUND OF THE INVENTION

Purine compounds, acting via cell surface purinoceptors, have been implicated as having a variety of physiological and pathological roles. ATP, and to a lesser extent, adenosine, can stimulate sensory nerve endings resulting in intense pain and a pronounced increase in sensory nerve discharge. ATP receptors have been classified into two major families, the P2Y- and P2X-purinoreceptors, on the basis of the molecular structure, transduction mechanisms, and pharmacological characterization. The P2Y-purinoceptors are G-protein coupled receptors, while the P2X-purinoceptors are a family of ATP-gated cation channels. Purinoceptors, in particular, P2X receptors, can form homomultimers or heteromultimers. To date, cDNAs for multiple P2X receptor subtypes (including six homologous receptors: P2X1, P2X2, P2X3, P2X4, P2X5 and P2X7; and three heterologous receptors: P2X2/3, P2X4/6 and P2X1/5) have been cloned. The structure and chromosomal mapping of mouse genomic P2X3 receptor subunits have also been reported.

Studies have shown that P2X3 and/or P2X2/3 receptor antagonists can be used to treat diseases such as pain, etc. The applicant has identified diaminopyrimidine compounds, specifically 5-((2-ethynyl-5-isopropylpyridin-4-yl)oxy)pyrimidine-2,4-diamine, which can be used as effective P2X3 and/or P2X2/3 receptor antagonists (see PCT/CN2018/112829, which is incorporated herein by reference in its entirety).

SUMMARY OF THE INVENTION

In one aspect, the present invention provides crystalline forms of compound A (5-((2-ethynyl-5-isopropylpyridin-4-yl)oxy)pyrimidine-2,4-diamine) as shown below or a hydrate thereof:

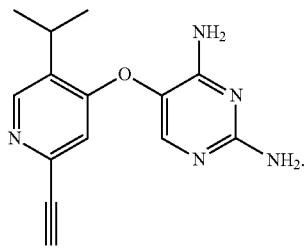

Compound A

The preferred crystalline forms of the present invention not only have an excellent effect in preventing or treating a disease mediated by the P2X3 and/or P2X2/3 receptor antagonist, but also have other advantages. For example, the preferred crystalline forms of the present invention have excellent physical properties (including solubility, dissolution rate, light resistance, low hygroscopicity, high temperature resistance, high humidity resistance, fluidity, and the like), and the preferred crystalline forms of the present invention may have superior properties in terms of bioavailability, physical and/or chemical stability, and ease of preparation. The preferred crystalline forms of the present invention have good powder properties, are more suitable and convenient for mass production and for forming a formulation, can reduce irritation and enhance absorption, solve problems in metabolic rates, significantly decrease toxicity resulted from drug accumulation, improve safety, and effectively ensure the quality and efficacy of the pharmaceutical products.

In another aspect, the present invention provides methods for preparing the crystalline forms of the present invention.

In another aspect, the present invention provides a pharmaceutical composition comprising any one or more of the crystalline forms of the present invention and one or more pharmaceutically acceptable carriers.

In another aspect, the present invention provides use of the crystalline form of the present invention in the manufacture of a medicament for the treatment of a disease mediated by a P2X3 and/or P2X2/3 receptor antagonist.

DETAILED DESCRIPTION OF THE INVENTION

Definitions

Figure 1:
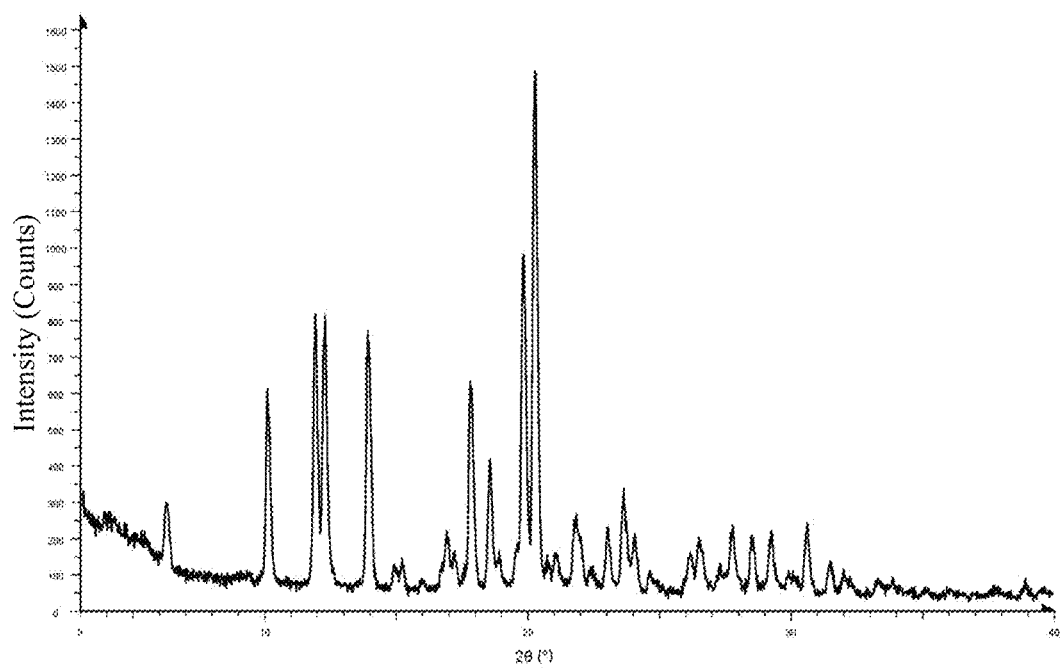
FIG. 1 is an X-ray powder diffraction pattern of crystalline form I of compound A anhydrate.

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that most of the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

The word "about" as used herein refers to, as appreciated by a person skilled in the art, a range within the acceptable standard error of a value, such as ±0.05, ±0.1, ±0.2, ±0.3, ±1, ±2 or ±3, etc.

The term "solid form" as used herein includes all solid forms of compound A or any hydrate thereof, such as a crystalline form or amorphous form.

The term "amorphous" as used herein refers to any solid substance which lacks order in three dimensions. In some instances, amorphous solids may be characterized by known techniques, including XRPD crystallography, solid state nuclear magnet resonance (ssNMR) spectroscopy, DSC, or some combination of these techniques. As illustrated below, amorphous solids give diffuse XRPD patterns, typically comprised of one or two broad peaks (i.e., peaks having base widths of about 5° 2θ or greater).

The term "crystalline form" or "crystal" as used herein refers to any solid substance exhibiting three-dimensional order, which in contrast to an amorphous solid substance, gives a distinctive XRPD pattern with sharply defined peaks.

The term "X-ray powder diffraction pattern (XRPD pattern)" as used herein refers to the experimentally observed diffractogram or parameters derived therefrom. XRPD patterns are usually characterized by peak positions (abscissa) and peak intensities (ordinate).

The term "2θ" as used herein refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific solid form is intended to mean the 2θ values (in degrees) as measured using the X-ray diffraction experimental conditions as described herein. For example, as described herein, Cu-Kα (Kα1 (Å): 1.540598 and Kα2 (Å): 1.544426 Å) was used as the source of radiation.

As used herein, "I %" refers to the percentage of peak intensity.

The term "differential scanning calorimetry (DSC) graph" as used herein refers to a curve recorded on a differential scanning calorimeter. Unless otherwise specified, the temperature mentioned when describing the characteristic peak in a DSC graph refers to the onset temperature of the peak.

The term "thermogravimetric analysis (TGA) graph" as used herein refers to a curve recorded on a thermogravimetric analyzer.

As used herein, the term "essentially the same" with reference to X-ray diffraction peak positions means that typical peak position and intensity variability are taken into account. For example, one skilled in the art will appreciate that the peak positions (2θ) will show some variability, typically as much as 0.1 to 0.2 degree, as well as on the apparatus being used to measure the diffraction. Further, one skilled in the art will appreciate that relative peak intensities will show inter-apparatus variability as well as variability due to degree of crystallinity, preferred orientation, prepared sample surface, and other factors known to those skilled in the art. Similarly, as used herein, "essentially the same" with reference to the DSC graph is intended to also encompass the variabilities associated with these analytical techniques, which are known to those of skill in the art. For example, a differential scanning calorimetry graph will typically have a variability of up to ±0.2° C. for well defined peaks, and even larger for broad lines (e.g., up to ±1° C.).

The liquid nuclear magnetic resonance spectrum in the present application is preferably collected on a Bruker 400M nuclear magnetic resonance spectrometer, with DMSO-d6 as the solvent, unless otherwise stated.

The polarization microscopy data in the present application is preferably collected on Polarizing Microscope ECLIPSE LV100POL (Nikon, JPN).

Numerical ranges (e.g., "1 to 10", "1 to 6", "2 to 10", "2 to 6", "3 to 10", "5 to 10", "3 to 6"), etc. as used herein encompass any point within the numerical range (for example, 1, 2, 3, 4, 5, 6, 7, 8, 9, or 10).

The prepared salt or crystalline form thereof may be recovered by methods including decantation, centrifugation, evaporation, gravity filtration, suction filtration, or any other technique for the recovery of solids under pressure or under reduced pressure. The recovered solid may optionally be dried. "Drying" in the present invention is carried out under reduced pressure (preferably in vacuum) until the residual solvent content is lowered within the limits given in the International Conference on Harmonisation of Technical Requirements for Registration of Pharmaceuticals for Human Use ("ICH") guidelines. The residual solvent content depends on the type of the solvent, but does not exceed about 5000 ppm, or preferably about 4000 ppm, or more preferably about 3000 ppm. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure (preferably in vacuum) for any desired period (e.g., about 1, 2, 3, 5, 10, 15, 20, 24 hours or overnight) until the desired result is achieved, as long as the salt is not degraded in quality. The drying can be carried out any desired times until the desired product quality is achieved. The dried product may optionally be subjected to a size reduction procedure to produce desired particle sizes Milling or micronization may be performed before drying, or after the completion of drying of the product. Techniques that may be used for particle size reduction include, without limitation, ball, roller and hammer milling, and jet milling.

The term "anhydrate" as used herein preferably means a crystalline form wherein no water molecule is comprised as a structural element.

Crystalline Form and Preparation Method Therefor

In an embodiment, the present invention provides crystalline form I of compound A anhydrate:

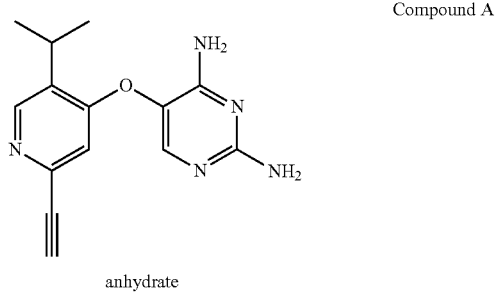 [SMILES: C#Cc1cc(Oc2cnc(N)nc2N)c(C(C)C)cn1]

Compound A anhydrate the crystalline form I has an XRPD pattern comprising characteristic peaks at diffraction angles (2θ) of about 11.9±0.2°, 12.3±0.2°, 13.9±0.2°, 19.8±0.2° and 20.3±0.2°.

In a preferred embodiment, the crystalline form I has an XRPD pattern comprising characteristic peaks at diffraction angles (2θ) of about 10.1±0.2°, 11.9±0.2°, 12.3±0.2°, 13.9±0.2°, 17.8±0.2°, 18.6±0.2°, 19.8±0.2° and 20.3±0.2°.

In a more preferred embodiment, the crystalline form I has an XRPD pattern comprising characteristic peaks at diffraction angles (2θ) of about 6.2±0.2°, 10.1±0.2°, 11.9±0.2°, 12.3±0.2°, 13.9±0.2°, 16.9±0.2°, 17.8±0.2°, 18.6±0.2°, 19.8±0.2°, 20.3±0.2°, 21.8±0.2°, 23.0±0.2°, 23.6±0.2°, 24.1±0.2°, 26.2±0.2°, 26.5±0.2°, 27.8±0.2°, 28.5±0.2°, 29.3±0.2° and 30.6±0.2°.

In a more preferred embodiment, the crystalline form I has an XRPD pattern comprising peaks at the following diffraction angles (2θ):

| Peak No. | 2θ (°) ± 0.2° | I % |
|---|---|---|
| 1 | 6.2° | 19.7 |
| 2 | 9.4° | 6.8 |
| 3 | 10.1° | 40.9 |
| 4 | 11.9° | 54.8 |
| 5 | 12.3° | 54.7 |
| 6 | 13.9° | 51.6 |
| 7 | 14.9° | 8.1 |
| 8 | 15.2° | 9.5 |
| 9 | 16.0° | 5.6 |
| 10 | 16.9° | 14.7 |
| 11 | 17.2° | 10.8 |
| 12 | 17.8° | 41.5 |
| 13 | 18.6° | 27.9 |
| 14 | 18.9° | 11.1 |
| 15 | 19.8° | 65.9 |
| 16 | 20.3° | 100 |
| 17 | 20.7° | 10.2 |
| 18 | 21.1° | 10.5 |
| 19 | 21.8° | 17.7 |
| 20 | 22.4° | 7.9 |
| 21 | 23.0° | 15.4 |
| 22 | 23.6° | 22.5 |
| 23 | 24.1° | 14.4 |
| 24 | 24.6° | 7.0 |
| 25 | 26.2° | 10.6 |
| 26 | 26.5° | 13.4 |
| 27 | 27.3° | 8.5 |
| 28 | 27.8° | 15.6 |
| 29 | 28.5° | 13.8 |
| 30 | 29.3° | 14.8 |
| 31 | 29.9° | 7.0 |
| 32 | 30.6° | 16.0 |
| 33 | 31.5° | 9.0 |
| 34 | 32.0° | 7.4 |
| 35 | 32.2° | 6.0 |
| 36 | 33.3° | 5.6 |
| 37 | 33.9° | 6.0 |
| 38 | 35.2° | 3.4 |
| 39 | 38.9° | 5.7 |
| 40 | 39.6° | 3.2 |

In a more preferred embodiment, the crystalline form I has an XRPD pattern comprising peaks at diffraction angles (2θ) essentially the same as shown in FIG. 1. In the most preferred embodiment, the XRPD peak positions of crystalline form I are essentially the same as shown in FIG. 1.

In a more preferred embodiment, the crystalline form I has a DSC graph comprising endothermic/exothermic peaks at about 245/255° C.

In a more preferred embodiment, in a thermogravimetric analysis, the crystalline form I has a weight loss of about 0.1% when heated to about 100-150° C.

Figure 2:
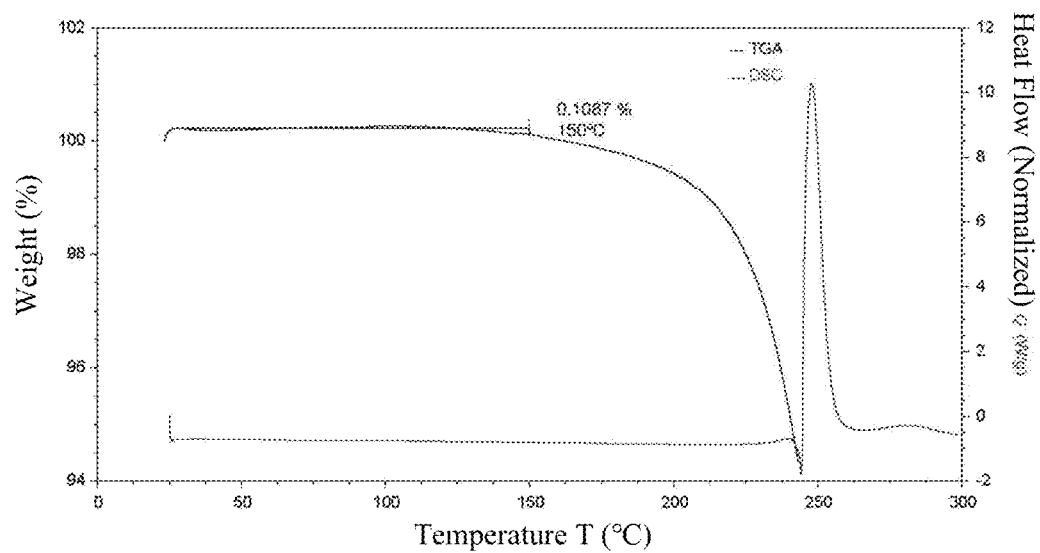
FIG. 2 is a differential scanning calorimetry (DSC) graph and a thermogravimetric analysis (TGA) graph of crystalline form I of compound A anhydrate.

In a more preferred embodiment, the crystalline form I has a DSC-TGA graph comprising characteristic peaks essentially the same as shown in FIG. 2. In the most preferred embodiment, the crystalline form I has a DSC-TGA graph essentially the same as shown in FIG. 2.

Figure 3:
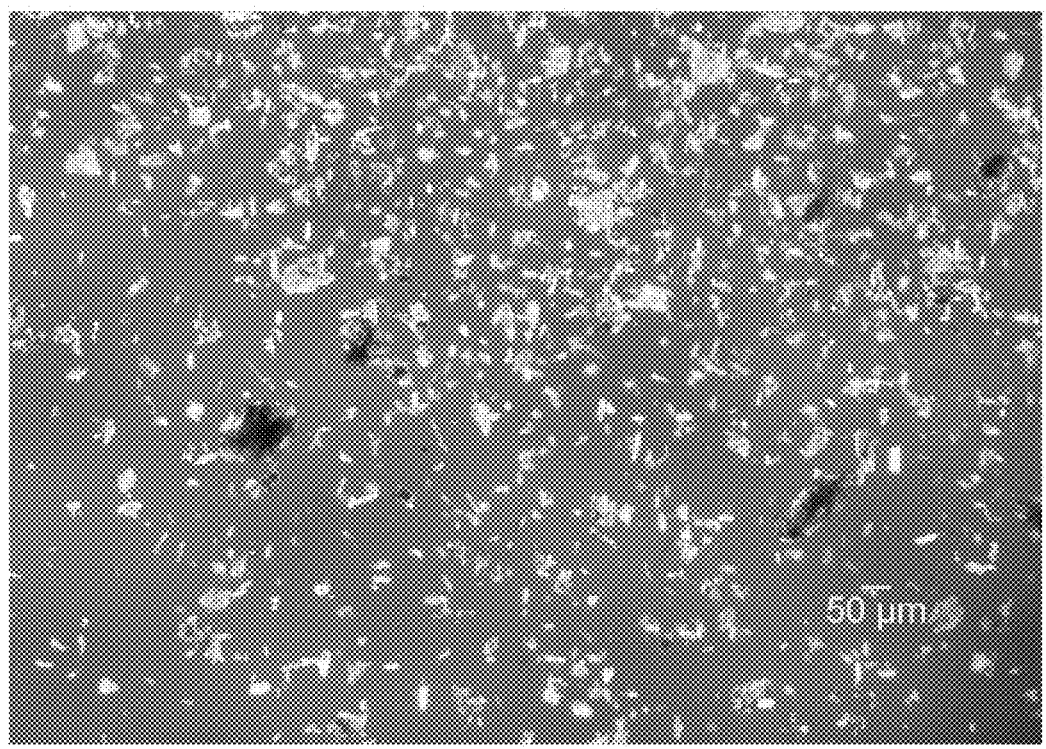
FIG. 3 is a scanning electron microscope image of crystalline form I of compound A anhydrate.

In a more preferred embodiment, the crystalline form I has a scanning electron microscope image essentially the same as shown in FIG. 3.

In some preferred embodiments, the present invention provides a method for preparing crystalline form I, comprising the following steps:

1) adding compound A to water, followed by addition of an acid (e.g., an organic acid (such as acetic acid or trifluoroacetic acid) or an inorganic acid (such as hydrochloric acid or sulfuric acid), preferably hydrochloric acid), stirring to dissolve compound A and obtain a solution, which is optionally filtered to obtain a filtrate;

2) adding a base (e.g., sodium hydroxide, potassium hydroxide or ammonia) to the solution or filtrate obtained in step 1), and collecting the precipitated solid by filtration; and 3) adding the obtained solid to water and stirring (e.g., for 0.5-5 hours, preferably 1-3 hours), filtering to collect the solid, which is optionally dried to obtain crystalline form I.

In some preferred embodiments, the present invention provides a method for preparing crystalline form I, comprising dissolving compound A in a good solvent (at room temperature or under heating (e.g., heating to 30-60° C., preferably 50° C.)), to form a solution (the mixture may be filtered as needed to provide a solution), then adding an anti-solvent thereto, and stirring (the addition of the anti-solvent and the stirring may be carried out at room temperature or under cooling (e.g., cooling to 0-10° C., preferably 5° C.)) to allow the precipitation of a solid, which is filtered to obtain the crystalline form.

In some preferred embodiments, the good solvent is an ether having 3-10 carbon atoms, preferably a cyclic ether, such as furans (including tetrahydrofurans) and dioxanes, preferably is tetrahydrofuran, 2-methyltetrahydrofuran or dioxane; and the anti-solvent is a hydrocarbon having 5-10 carbon atoms (including alkanes, halogenated alkanes, alkenes, alkynes and aromatic hydrocarbons, including but not limited to dichloromethane, trichloromethane (chloroform), n-hexane, n-heptane and toluene) or an ether having 2-6 carbon atoms (preferably linear ethers, such as diethyl ether, diisopropyl ether or methyl tert-butyl ether).

In some preferred embodiments, the weight/volume ratio (g/mL) of compound A to the good solvent is about 1:(30-120), preferably about 1:40 or 1:100.

In some preferred embodiments, the volume ratio of the good solvent to the anti-solvent is about 1:1 to 1:5.

In another embodiment, the present invention provides crystalline form II of compound A monohydrate:

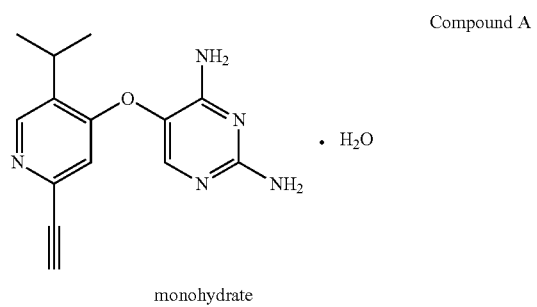 [SMILES: C#Cc1cc(Oc2cnc(N)nc2N)c(C(C)C)cn1 ; O]

Compound A

· $H_2O$ monohydrate the crystalline form II has an XRPD pattern comprising characteristic peaks at diffraction angles (2θ) of about 13.0±0.2°, 19.5±0.2° and 19.9±0.2°.

In a preferred embodiment, the crystalline form II has an XRPD pattern comprising characteristic peaks at diffraction angles (2θ) of about 9.6±0.2°, 13.0±0.2°, 19.5±0.2°, 19.9±0.2° and 22.7±0.2°.

In a more preferred embodiment, the crystalline form II has an XRPD pattern comprising characteristic peaks at diffraction angles (2θ) of about 9.6±0.2°, 10.9±0.2°, 13.0±0.2°, 14.9±0.2°, 15.8±0.2°, 16.8±0.2°, 19.5±0.2°, 19.9±0.2°, 22.7±0.2°, 23.7±0.2°, 25.2±0.2°, 26.0±0.2°, 28.5±0.2°, 29.0±0.2°, 30.0±0.2° and 32.5±0.2°.

In a more preferred embodiment, the crystalline form II has an XRPD pattern comprising peaks at the following diffraction angles (2θ):

| Peak No. | 2θ (°) ± 0.2° | I % |
|---|---|---|
| 1 | 9.6° | 27.3 |
| 2 | 10.9° | 22.0 |
| 3 | 13.0° | 100 |
| 4 | 13.3° | 23.3 |
| 5 | 14.9° | 14.8 |
| 6 | 15.8° | 25.0 |
| 7 | 16.8° | 18.1 |
| 8 | 17.7° | 6.5 |
| 9 | 19.5° | 70.8 |
| 10 | 19.9° | 82.2 |
| 11 | 21.2° | 8.5 |
| 12 | 22.1° | 7.8 |
| 13 | 22.7° | 42.1 |
| 14 | 23.7° | 16.1 |
| 15 | 24.5° | 8.2 |
| 16 | 25.2° | 15.4 |
| 17 | 25.6° | 10.6 |
| 18 | 26.0° | 13.0 |
| 19 | 26.8° | 6.6 |
| 20 | 28.5° | 17.1 |
| 21 | 29.0° | 23.7 |
| 22 | 30.0° | 13.1 |
| 23 | 31.0° | 4.2 |
| 24 | 32.5° | 7.2 |
| 25 | 33.0° | 5.3 |
| 26 | 33.6° | 4.1 |
| 27 | 34.7° | 3.6 |
| 28 | 35.6° | 4.3 |
| 29 | 36.3° | 3.7 |
| 30 | 37.1° | 4.2 |

Figure 4:
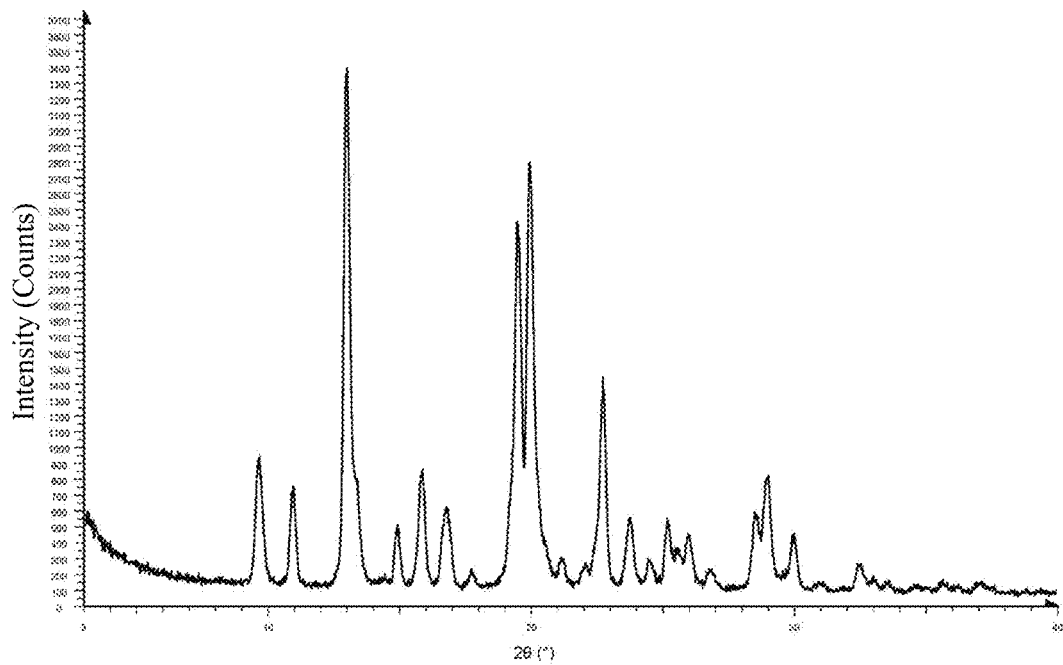
FIG. 4 is an X-ray powder diffraction pattern of crystalline form II of compound A monohydrate.

In a more preferred embodiment, the crystalline form II has an XRPD pattern comprising peaks at diffraction angles (2θ) essentially the same as shown in FIG. 4. In the most preferred embodiment, the XRPD peak positions of crystalline form II are essentially the same as shown in FIG. 4.

In a more preferred embodiment, the crystalline form II has a DSC graph comprising an endothermic peak at about 73.9° C. and endothermic/exothermic peaks at about 245/255° C.

In a more preferred embodiment, in a thermogravimetric analysis, the crystalline form II has a weight loss of about 6.2% when heated to about 100° C.

Figure 5:
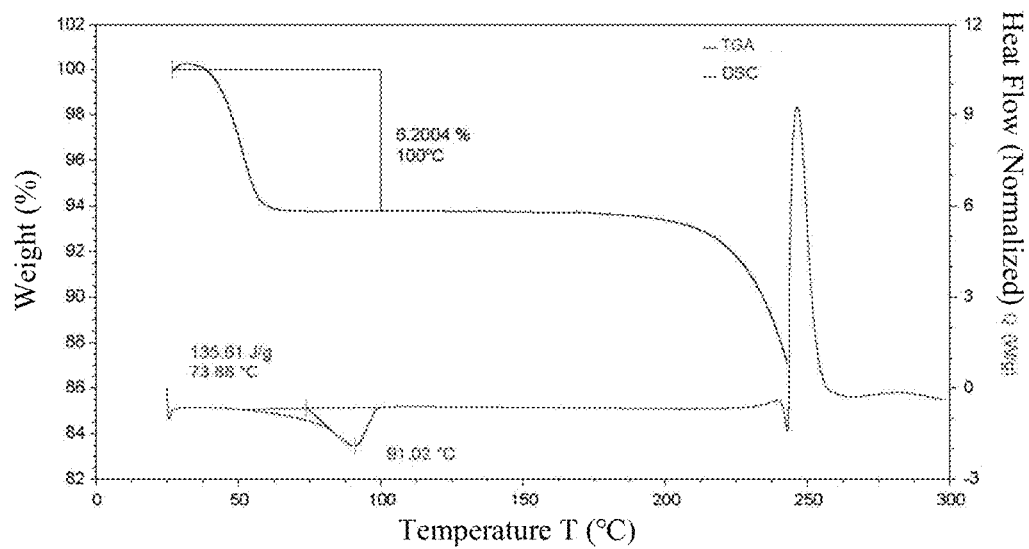
FIG. 5 is a differential scanning calorimetry (DSC) graph and a thermogravimetric analysis (TGA) graph of crystalline form II of compound A monohydrate.

In a more preferred embodiment, the crystalline form II has a DSC-TGA graph comprising characteristic peaks essentially the same as shown in FIG. 5. In the most preferred embodiment, the crystalline form II has a DSC-TGA graph essentially the same as shown in FIG. 5.

In some preferred embodiments, the present invention provides a method for preparing crystalline form II, comprising suspending compound A in an aqueous alcohol solvent (preferably an alcohol having 1-6 carbon atoms, including but not limited to methanol, ethanol, 1-propanol (n-propanol), 2-propanol (isopropanol), 1-butanol, 2-butanol and tert butanol) and stirring (e.g., at room temperature) (e.g., for 1-5 days, such as 3 days), filtering to obtain the crystalline form.

In some preferred embodiments, the weight/volume ratio (g/mL) of compound A to the aqueous alcohol solvent is about 1:(30-100), preferably about 1:50.

In another embodiment, the present invention provides crystalline form III of compound A hemihydrate:

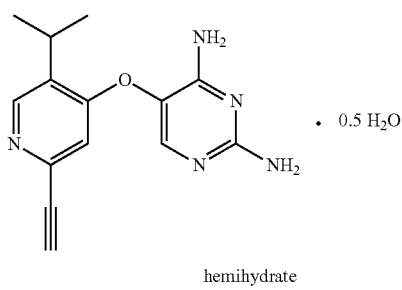

Compound A

· 0.5 H₂O hemihydrate the crystalline form III has an XRPD pattern comprising characteristic peaks at diffraction angles (2θ) of about 10.8±0.2° and 20.5±0.2°.

In a preferred embodiment, the crystalline form III has an XRPD pattern comprising characteristic peaks at diffraction angles (2θ) of about 10.8±0.2°, 19.3±0.2°, 20.5±0.2°, 21.7±0.2° and 26.9±0.2°.

In a more preferred embodiment, the crystalline form III has an XRPD pattern comprising characteristic peaks at diffraction angles (2θ) of about 10.8±0.2°, 13.0±0.2°, 15.0±0.2°, 15.4±0.2°, 16.5±0.2°, 17.3±0.2°, 19.3±0.2°, 19.9±0.2°, 20.5±0.2°, 21.7±0.2°, 23.3±0.2°, 25.1±0.2°, 26.5±0.2°, 26.9±0.2°, 28.7±0.2° and 32.2±0.2°.

In a more preferred embodiment, the crystalline form III has an XRPD pattern comprising peaks at the following diffraction angles (2θ):

| Peak No. | 2θ (°) ± 0.2° | I % |
|---|---|---|
| 1 | 8.4° | 6.5 |
| 2 | 10.8° | 100 |
| 3 | 13.0° | 10.9 |
| 4 | 15.0° | 19.3 |
| 5 | 15.4° | 9.7 |
| 6 | 16.5° | 19.7 |
| 7 | 16.8° | 7.0 |
| 8 | 17.3° | 10.3 |
| 9 | 19.3° | 27.9 |
| 10 | 19.9° | 16.8 |
| 11 | 20.5° | 86.6 |
| 12 | 21.7° | 40.6 |
| 13 | 23.0° | 9.7 |
| 14 | 23.3° | 11.7 |
| 15 | 23.7° | 6.7 |
| 16 | 24.4° | 6.2 |
| 17 | 25.1° | 10.9 |
| 18 | 25.7° | 6.6 |
| 19 | 26.2° | 9.3 |
| 20 | 26.5° | 18.4 |
| 21 | 26.9° | 30.9 |
| 22 | 28.7° | 11.8 |
| 23 | 29.6° | 7.2 |
| 24 | 30.8° | 4.9 |
| 25 | 31.5° | 4.1 |
| 26 | 32.2° | 10.4 |
| 27 | 32.6° | 6.4 |
| 28 | 34.1° | 5.6 |
| 29 | 35.0° | 5.8 |

Figure 6:
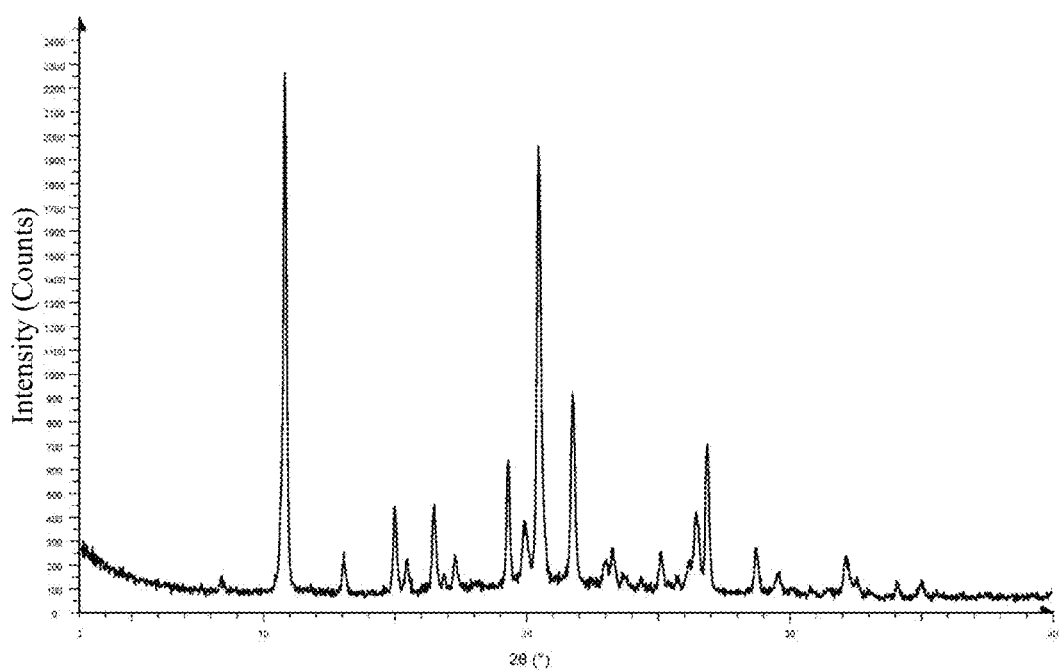
FIG. 6 is an X-ray powder diffraction pattern of crystalline form III of compound A hemihydrate.

In a more preferred embodiment, the crystalline form III has an XRPD pattern comprising peaks at diffraction angles (2θ) essentially the same as shown in FIG. 6. In the most preferred embodiment, the XRPD peak positions of crystalline form III are essentially the same as shown in FIG. 6.

In a more preferred embodiment, the crystalline form III has a DSC graph comprising an endothermic peak at about 62.2° C. and endothermic/exothermic peaks at about 245/255° C.

In a more preferred embodiment, in a thermogravimetric analysis, the crystalline form III has a weight loss of about 3.6% when heated to about 80° C.

Figure 7:
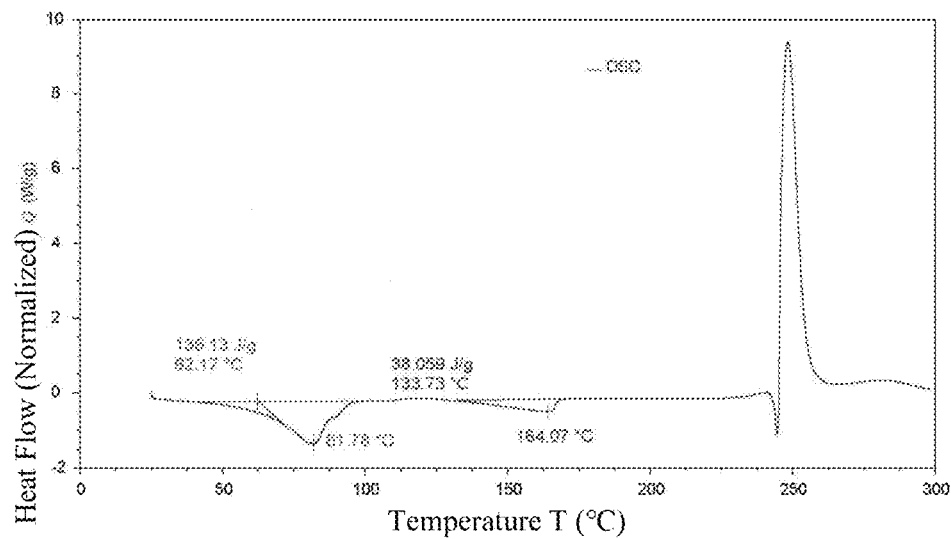
FIG. 7 is a differential scanning calorimetry (DSC) graph of crystalline form III of compound A hemihydrate.

In a more preferred embodiment, the crystalline form III has a DSC graph comprising characteristic peaks essentially the same as shown in FIG. 7. In the most preferred embodiment, the crystalline form III has a DSC graph essentially the same as shown in FIG. 7.

In some preferred embodiments, the present invention provides a method for preparing crystalline form III, comprising dissolving compound A in a good solvent (e.g., at room temperature), to form a solution (the mixture may be filtered as needed to provide a solution), then adding an anti-solvent thereto, and stirring (the addition of the anti-solvent and the stirring is carried out e.g., at room temperature) to allow the precipitation of a solid, which is filtered to obtain the crystalline form.

In some preferred embodiments, the good solvent is a sulfone or sulfoxide having 2-10 carbon atoms, including but not limited to dimethyl sulfoxide; and the anti-solvent is preferably water.

In some preferred embodiments, the weight/volume ratio (g/mL) of compound A to the good solvent is about 1:(1-20), preferably about 1:12.5.

In some preferred embodiments, the volume ratio of the good solvent to the anti-solvent is about 1:1 to 1:3.

In another embodiment, the present invention provides crystalline form IV of compound A sesquihydrate:

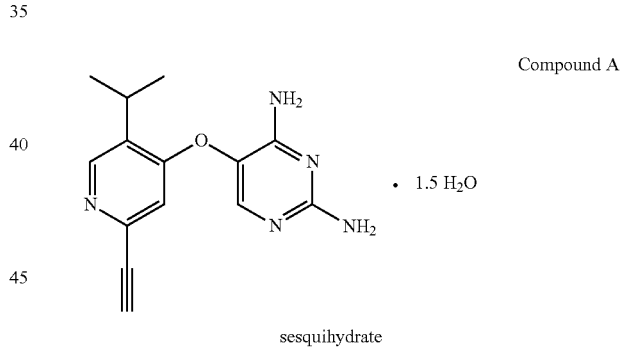

Compound A

· 1.5 H₂O sesquihydrate the crystalline form IV has an XRPD pattern comprising characteristic peaks at diffraction angles (2θ) of about 12.3±0.2°, 21.3±0.2° and 24.1±0.2°.

In a preferred embodiment, the crystalline form IV has an XRPD pattern comprising characteristic peaks at diffraction angles (2θ) of about 12.3±0.2°, 12.6±0.2°, 17.2±0.2°, 20.0±0.2°, 20.6±0.2°, 21.3±0.2°, 23.8±0.2°, 24.1±0.2°, 25.0±0.2° and 27.9±0.2°.

In a more preferred embodiment, the crystalline form IV has an XRPD pattern comprising characteristic peaks at diffraction angles (2θ) of about 12.3±0.2°, 12.6±0.2°, 14.3±0.2°, 17.2±0.2°, 20.0±0.2°, 20.6±0.2°, 21.3±0.2°, 23.2±0.2°, 23.8±0.2°, 24.1±0.2°, 25.0±0.2°, 25.7±0.2°, 27.9±0.2°, 31.2±0.2° and 31.7±0.2°.

In a more preferred embodiment, the crystalline form IV has an XRPD pattern comprising peaks at the following diffraction angles (2θ):

| Peak No. | 2θ (°) ± 0.2° | I % |
| --- | --- | --- |
| 1 | 7.4° | 9.4 |
| 2 | 10.0° | 9.1 |
| 3 | 11.9° | 8.0 |
| 4 | 12.3° | 100 |
| 5 | 12.6° | 42.7 |
| 6 | 13.9° | 8.5 |
| 7 | 14.3° | 16.3 |
| 8 | 14.9° | 6.3 |
| 9 | 16.6° | 6.9 |
| 10 | 17.2° | 37.1 |
| 11 | 17.8° | 11.0 |
| 12 | 18.0° | 8.4 |
| 13 | 18.5° | 8.5 |
| 14 | 18.8° | 5.3 |
| 15 | 20.0° | 32.1 |
| 16 | 20.2° | 16.5 |
| 17 | 20.6° | 33.4 |
| 18 | 21.3° | 50.6 |
| 19 | 22.0° | 8.5 |
| 20 | 23.2° | 18.7 |
| 21 | 23.8° | 36.1 |
| 22 | 24.1° | 57.5 |
| 23 | 25.0° | 30.2 |
| 24 | 25.7° | 18.9 |
| 25 | 26.1° | 13.9 |
| 26 | 26.4° | 9.6 |
| 27 | 27.4° | 11.6 |
| 28 | 27.9° | 40.3 |
| 29 | 28.5° | 7.1 |
| 30 | 28.8° | 8.5 |
| 31 | 30.0° | 8.6 |
| 32 | 31.2° | 18.0 |
| 33 | 31.7° | 17.7 |
| 34 | 32.9° | 7.4 |
| 35 | 33.2° | 10.7 |
| 36 | 33.6° | 9.4 |
| 37 | 34.2° | 5.3 |
| 38 | 35.6° | 5.4 |
| 39 | 36.6° | 5.9 |
| 40 | 37.1° | 6.2 |
| 41 | 38.1° | 5.2 |

Figure 8:
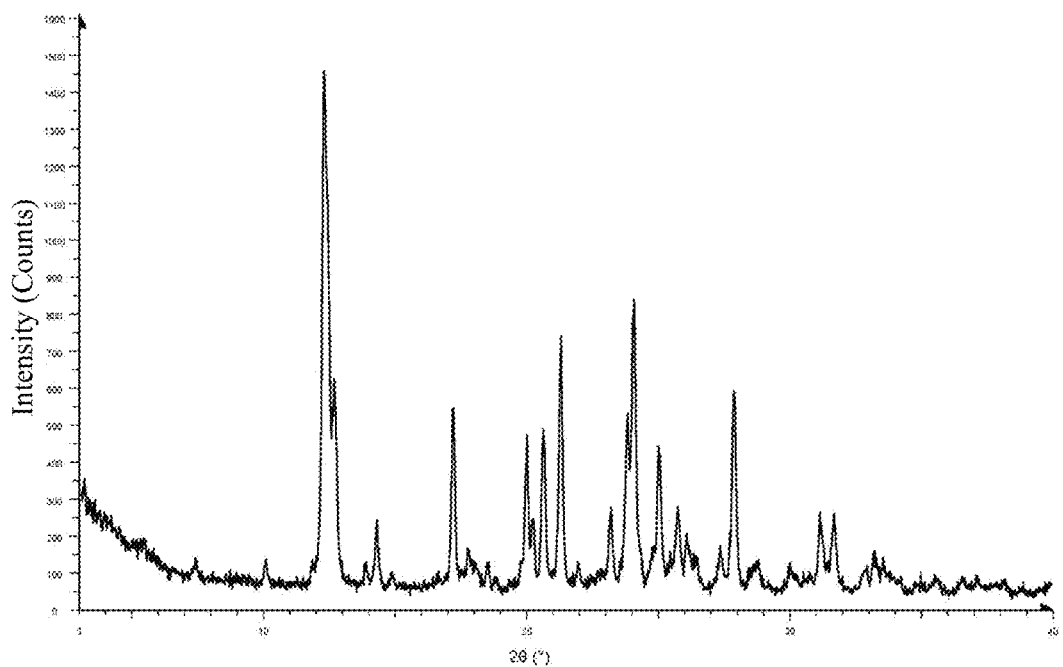
FIG. 8 is an X-ray powder diffraction pattern of crystalline form IV of compound A sesquihydrate.

In a more preferred embodiment, the crystalline form IV has an XRPD pattern comprising peaks at diffraction angles (2θ) essentially the same as shown in FIG. 8. In the most preferred embodiment, the XRPD peak positions of crystalline form IV are essentially the same as shown in FIG. 8.

In a more preferred embodiment, the crystalline form IV has a DSC graph comprising an endothermic peak at about 42.6° C., an endothermic peak at about 66.9° C. and endothermic/exothermic peaks at about 245/255° C.

In a more preferred embodiment, in a thermogravimetric analysis, the crystalline form IV has a weight loss of about 9.4% when heated to about 100° C.

Figure 9:
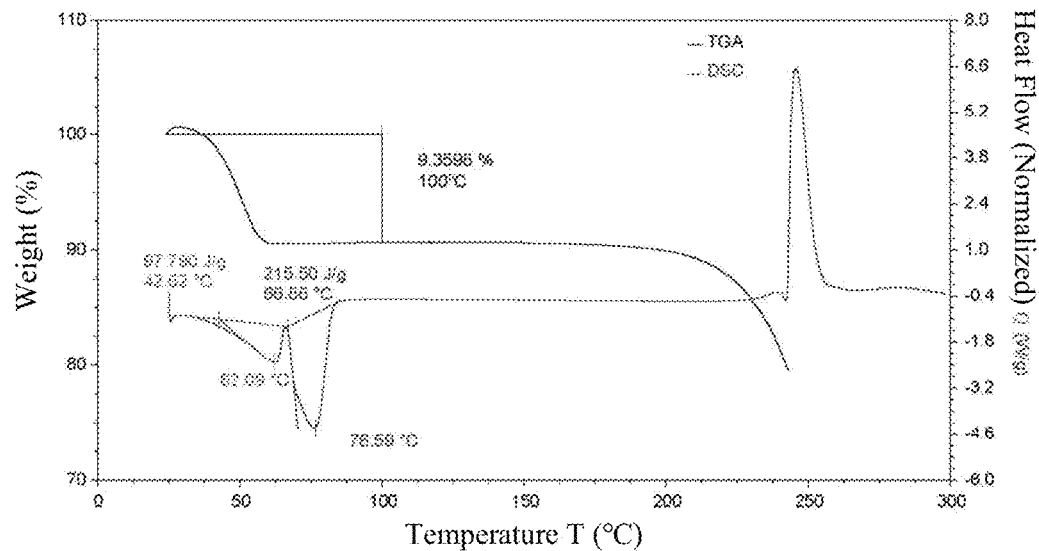
FIG. 9 is a differential scanning calorimetry (DSC) graph and a thermogravimetric analysis (TGA) graph of crystalline form IV of compound A sesquihydrate.

In a more preferred embodiment, the crystalline form IV has a DSC-TGA graph comprising characteristic peaks essentially the same as shown in FIG. 9. In the most preferred embodiment, the crystalline form IV has a DSC-TGA graph essentially the same as shown in FIG. 9.

In some preferred embodiments, the present invention provides a method for preparing crystalline form IV, comprising stirring compound A in water (for example, at room temperature, e.g., for 1-5 days, preferably 2-4 days), and filtering to obtain the crystalline form.

In some preferred embodiments, the weight/volume ratio (g/mL) of compound A to water is about 1:(30-100), preferably about 1:50.

In some preferred embodiments, the present invention provides a method for preparing crystalline form IV, comprising dissolving compound A in a good solvent (e.g., at room temperature), to form a solution (the mixture may be filtered as needed to provide a solution), then adding an anti-solvent thereto, and stirring (the addition of the anti-solvent and the stirring is carried out e.g., at room temperature) to allow the precipitation of a solid, which is filtered to obtain the crystalline form.

In some preferred embodiments, the good solvent is an ether having 3-10 carbon atoms, preferably a cyclic ether, such as furans (including tetrahydrofurans) and dioxanes, preferably is tetrahydrofuran, 2-methyltetrahydrofuran or dioxane; and the anti-solvent is preferably water.

In some preferred embodiments, the weight/volume ratio (g/mL) of compound A to the good solvent is about 1:(50-120), preferably about 1:100.

In some preferred embodiments, the volume ratio of the good solvent to the anti-solvent is about 1:1 to 1:5.

In another embodiment, the present invention provides crystalline form V of compound A monohydrate:

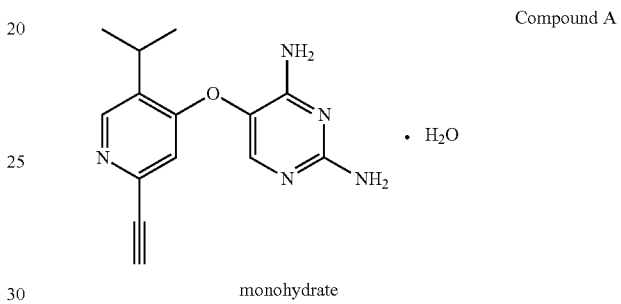

Compound A monohydrate the crystalline form V has an XRPD pattern comprising characteristic peaks at diffraction angles (2θ) of about 14.1±0.2°, 21.0±0.2° and 29.6±0.2°.

In a preferred embodiment, the crystalline form V has an XRPD pattern comprising characteristic peaks at diffraction angles (2θ) of about 8.7±0.2°, 9.4±0.2°, 11.9±0.2°, 14.1±0.2°, 15.8±0.2°, 16.8±0.2°, 18.9±0.2°, 19.9±0.2°, 20.6±0.2°, 21.0±0.2°, 22.5±0.2° and 29.6±0.2°.

In a more preferred embodiment, the crystalline form V has an XRPD pattern comprising characteristic peaks at diffraction angles (2θ) of about 8.7±0.2°, 9.4±0.2°, 11.6±0.2°, 11.9±0.2°, 12.4±0.2°, 14.1±0.2°, 14.5±0.2°, 15.8±0.2°, 16.2±0.2°, 16.8±0.2°, 17.6±0.2°, 18.2±0.2°, 18.9±0.2°, 19.9±0.2°, 20.6±0.2°, 21.0±0.2°, 22.5±0.2°, 23.0±0.2°, 23.6±0.2°, 24.4±0.2°, 25.2±0.2°, 27.0±0.2° and 29.6±0.2°.

In a more preferred embodiment, the crystalline form V has an XRPD pattern comprising peaks at the following diffraction angles (2θ):

| Peak No. | 2θ (°) ± 0.2° | I % |
| --- | --- | --- |
| 1 | 5.9° | 6.4 |
| 2 | 8.7° | 27.0 |
| 3 | 9.4° | 23.4 |
| 4 | 9.9° | 6.6 |
| 5 | 10.3° | 6.8 |
| 6 | 11.6° | 20.7 |
| 7 | 11.9° | 32.7 |
| 8 | 12.4° | 11.4 |
| 9 | 12.8° | 7.1 |
| 10 | 13.4° | 4.6 |
| 11 | 14.1° | 60.9 |
| 12 | 14.5° | 10.4 |
| 13 | 15.8° | 25.3 |
| 14 | 16.2° | 16.5 |
| 15 | 16.8° | 22.5 |

| Peak No. | 2θ (°) ± 0.2° | I % |
| --- | --- | --- |
| 16 | 17.6° | 16.8 |
| 17 | 18.2° | 13.7 |
| 18 | 18.9° | 29.5 |
| 19 | 19.4° | 9.5 |
| 20 | 19.9° | 24.1 |
| 21 | 20.6° | 29.1 |
| 22 | 21.0° | 100 |
| 23 | 21.4° | 12.8 |
| 24 | 22.1° | 9.6 |
| 25 | 22.5° | 22.5 |
| 26 | 23.0° | 14.4 |
| 27 | 23.4° | 11.3 |
| 28 | 23.6° | 19.9 |
| 29 | 23.9° | 11.9 |
| 30 | 24.4° | 18.5 |
| 31 | 24.7° | 14.3 |
| 32 | 25.2° | 16.2 |
| 33 | 25.6° | 6.5 |
| 34 | 26.4° | 8.7 |
| 35 | 26.6° | 8.0 |
| 36 | 27.0° | 16.7 |
| 37 | 27.4° | 6.5 |
| 38 | 27.8° | 9.2 |
| 39 | 28.1° | 7.7 |
| 40 | 28.5° | 7.7 |
| 41 | 28.8° | 6.5 |
| 42 | 29.6° | 46.4 |
| 43 | 30.1° | 8.0 |
| 44 | 31.1° | 4.1 |
| 45 | 31.7° | 6.0 |
| 46 | 32.6° | 6.2 |
| 47 | 32.9° | 7.0 |
| 48 | 33.1° | 6.3 |
| 49 | 34.0° | 4.3 |
| 50 | 34.7° | 4.5 |
| 51 | 37.0° | 3.5 |
| 52 | 38.5° | 5.1 |
| 53 | 39.7° | 3.9 |

Figure 10:
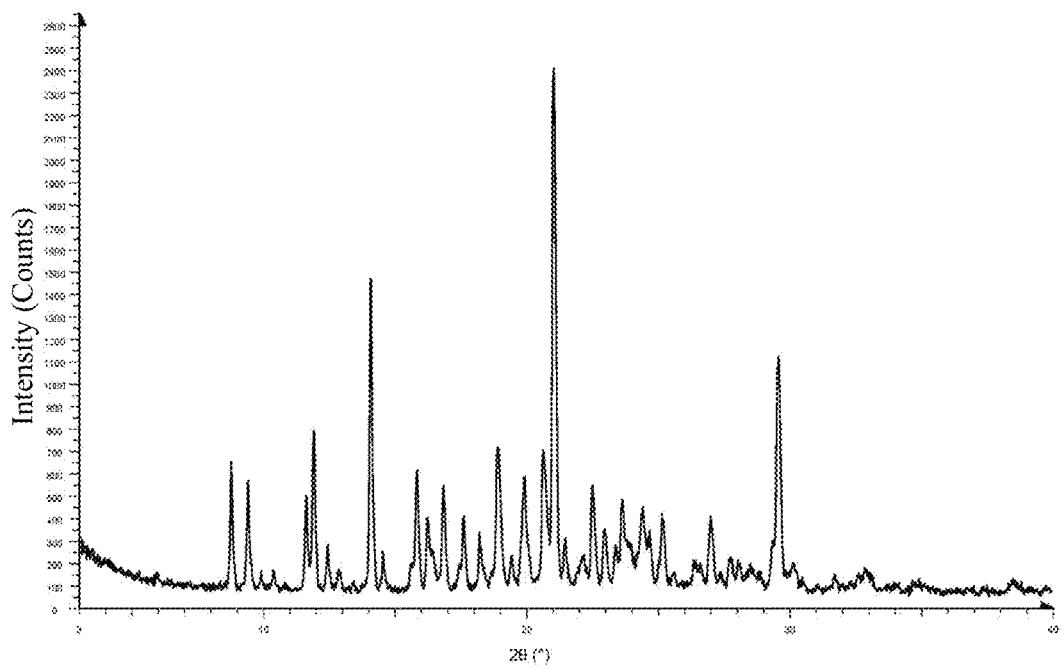
FIG. 10 is an X-ray powder diffraction pattern of crystalline form V of compound A monohydrate.

In a more preferred embodiment, the crystalline form V has an XRPD pattern comprising peaks at diffraction angles (2θ) essentially the same as shown in FIG. 10. In the most preferred embodiment, the XRPD peak positions of crystalline form V are essentially the same as shown in FIG. 10.

In a more preferred embodiment, the crystalline form V has a DSC graph comprising an endothermic peak at about 52.6° C. and endothermic/exothermic peaks at about 245/255° C.

In a more preferred embodiment, in a thermogravimetric analysis, the crystalline form V has a weight loss of about 6.8% when heated to about 80° C.

Figure 11:
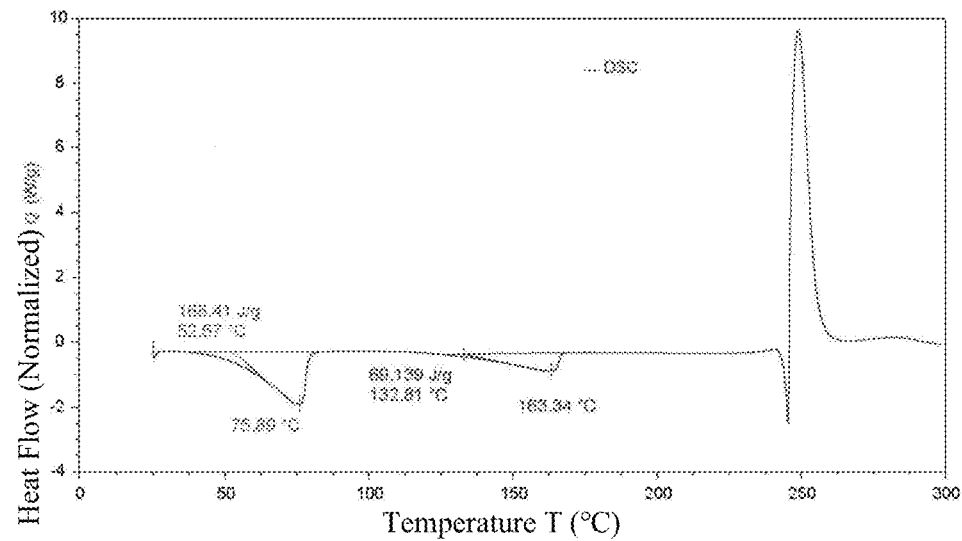
FIG. 11 is a differential scanning calorimetry (DSC) graph of crystalline form V of compound A monohydrate.

In a more preferred embodiment, the crystalline form V has a DSC graph comprising characteristic peaks essentially the same as shown in FIG. 11. In the most preferred embodiment, the crystalline form V has a DSC graph essentially the same as shown in FIG. 11.

In some preferred embodiments, the present invention provides a method for preparing crystalline form V, comprising dissolving compound A in a good solvent (e.g., at room temperature), to form a solution (the mixture may be filtered as needed to provide a solution), then adding an anti-solvent thereto, and stirring (the addition of the anti-solvent and the stirring is carried out e.g., at room temperature) to allow the precipitation of a solid, which is filtered to obtain the crystalline form.

In some preferred embodiments, the good solvent is a sulfone or sulfoxide having 2-10 carbon atoms, including but not limited to dimethyl sulfoxide; and the anti-solvent is preferably an aqueous alcohol solvent (preferably is an alcohol having 1-6 carbon atoms, including but not limited to methanol, ethanol, 1-propanol (n-propanol), 2-propanol (isopropanol), 1-butanol, 2-butanol and tert-butanol).

In some preferred embodiments, the weight/volume ratio (g/mL) of compound A to the good solvent is about 1:(1-20), preferably about 1:12.5.

In some preferred embodiments, the volume ratio of the good solvent to the anti-solvent is about 1:1 to 1:3.

In another embodiment, the present invention provides crystalline form VI of compound A monohydrate:

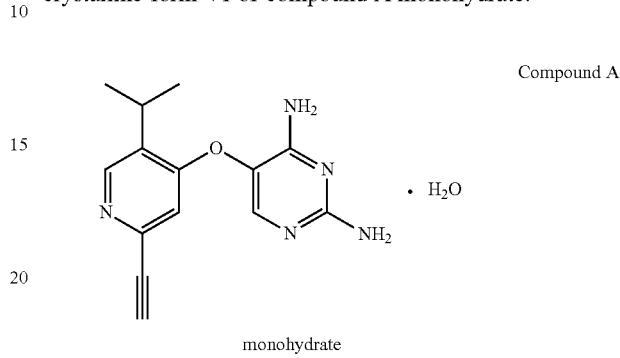

monohydrate the crystalline form VI has an XRPD pattern comprising characteristic peaks at diffraction angles (2θ) of about 10.4±0.2°, 12.1±0.2°, 16.6±0.2°, 20.7±0.2°, 22.8±0.2° and 27.3±0.2°.

In a preferred embodiment, the crystalline form VI has an XRPD pattern comprising characteristic peaks at diffraction angles (2θ) of about 8.7±0.2°, 10.4±0.2°, 12.1±0.2°, 15.4±0.2°, 16.6±0.2°, 19.5±0.2°, 20.7±0.2°, 21.2±0.2°, 22.8±0.2° and 27.3±0.2°.

In a more preferred embodiment, the crystalline form VI has an XRPD pattern comprising characteristic peaks at diffraction angles (2θ) of about 8.7±0.2°, 10.4±0.2°, 12.1±0.2°, 13.4±0.2°, 14.7±0.2°, 15.4±0.2°, 16.6±0.2°, 17.4±0.2°, 19.5±0.2°, 20.7±0.2°, 21.2±0.2°, 22.1±0.2°, 22.8±0.2°, 23.6±0.2°, 26.0±0.2°, 27.3±0.2°, 28.0±0.2° and 30.4±0.2°.

In a more preferred embodiment, the crystalline form VI has an XRPD pattern comprising peaks at the following diffraction angles (2θ):

| Peak No. | 2θ (°) ± 0.2° | I % |
| --- | --- | --- |
| 1 | 8.7° | 31.8 |
| 2 | 10.4° | 51.1 |
| 3 | 12.1° | 63.0 |
| 4 | 13.4° | 14.9 |
| 5 | 14.7° | 15.4 |
| 6 | 15.4° | 29.8 |
| 7 | 16.6° | 61.9 |
| 8 | 17.4° | 14.5 |
| 9 | 19.5° | 49.5 |
| 10 | 20.7° | 100 |
| 11 | 21.2° | 44.8 |
| 12 | 22.1° | 16.2 |
| 13 | 22.8° | 53.3 |
| 14 | 23.6° | 24.7 |
| 15 | 26.0° | 23.4 |
| 16 | 27.3° | 53.2 |
| 17 | 28.0° | 20.9 |
| 18 | 28.6° | 8.4 |
| 19 | 30.4° | 18.1 |
| 20 | 31.6° | 9.9 |
| 21 | 32.1° | 10.0 |
| 22 | 33.9° | 7.2 |
| 23 | 34.7° | 8.4 |
| 24 | 35.9° | 7.7 |

| Peak No. | 2θ (°) ± 0.2° | I % |
|---|---|---|
| 25 | 36.8° | 6.8 |
| 26 | 38.8° | 6.1 |

Figure 12:
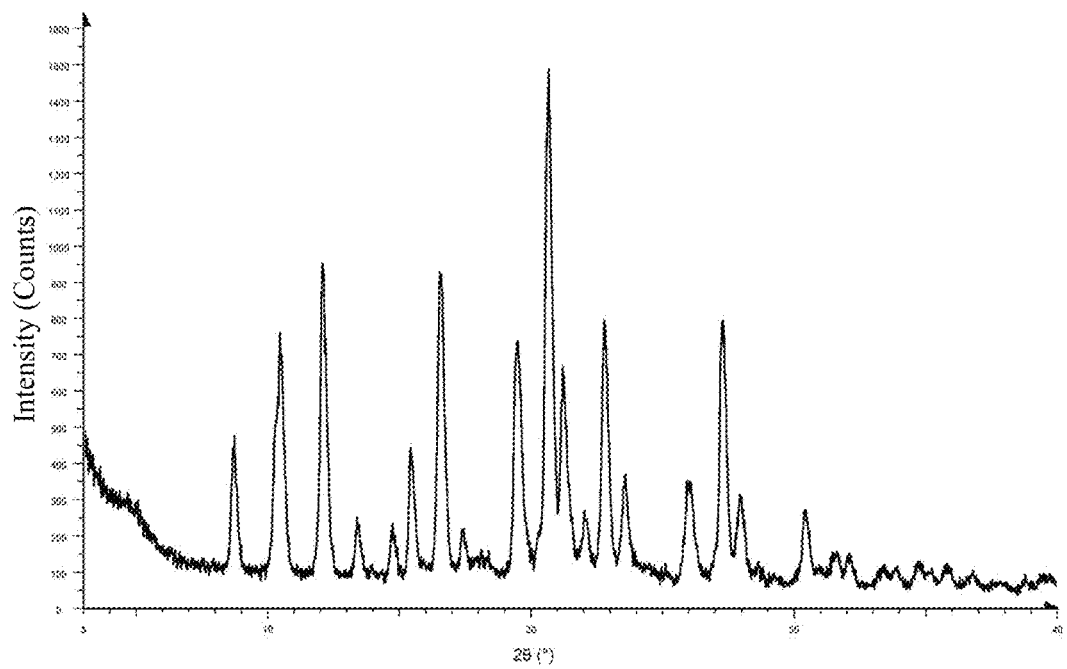
FIG. 12 is an X-ray powder diffraction pattern of crystalline form VI of compound A monohydrate.

In a more preferred embodiment, the crystalline form VI has an XRPD pattern comprising peaks at diffraction angles (2θ) essentially the same as shown in FIG. 12. In the most preferred embodiment, the XRPD peak positions of crystalline form VI are essentially the same as shown in FIG. 12.

In a more preferred embodiment, the crystalline form VI has a DSC graph comprising an endothermic peak at about 51.6° C., an endothermic peak at about 77.5° C., and endothermic/exothermic peaks at about 245/255° C.

Figure 13:
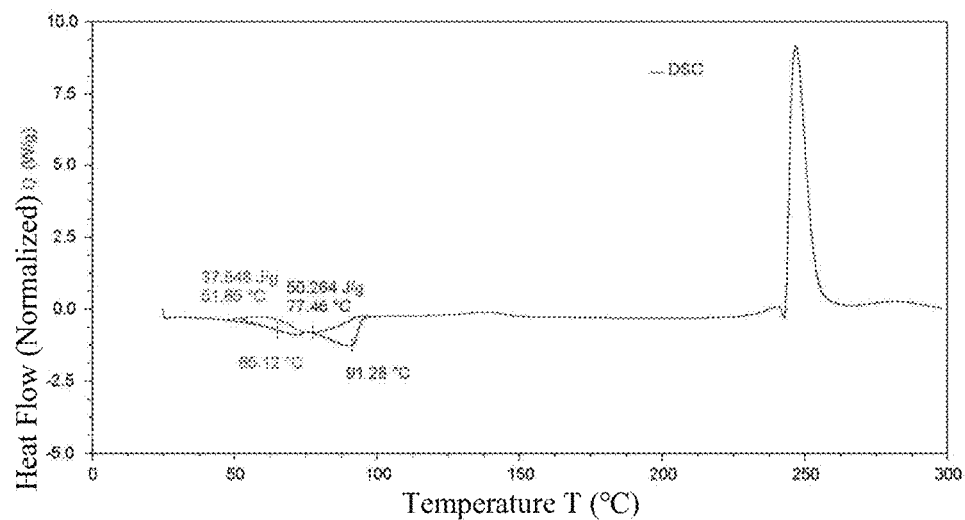
FIG. 13 is a differential scanning calorimetry (DSC) graph of crystalline form VI of compound A monohydrate.

In a more preferred embodiment, the crystalline form VI has a DSC graph comprising characteristic peaks essentially the same as shown in FIG. 13. In the most preferred embodiment, the crystalline form VI has a DSC graph essentially the same as shown in FIG. 13.

In some preferred embodiments, the present invention provides a method for preparing crystalline form VI, comprising stirring compound A (e.g., at room temperature) in a mixed solvent of a ketone solvent (e.g., a ketone having 3-6 carbon atoms, including but not limited to acetone, butanone, methyl ethyl ketone, methyl isobutyl ketone and diethyl ketone) and water (e.g., for 1-5 days), and filtering to obtain the crystalline form.

In some preferred embodiments, the volume ratio of the ketone solvent to water is about 10:1 to 1:1, preferably about 5:1 to 2:1.

In some preferred embodiments, the weight/volume ratio (g/mL) of compound A to the mixed solvent is about 1:(1-30), preferably about 1:20.

In another embodiment, the present invention provides crystalline form VII of compound A sesquihydrate:

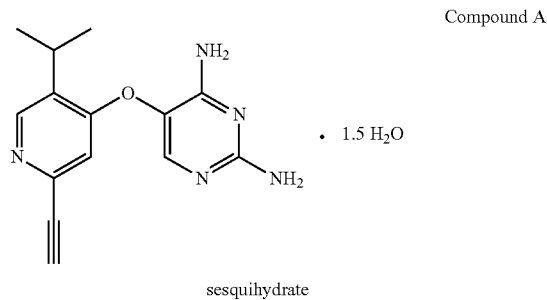 [SMILES: C#Cc1cc(Oc2cnc(N)nc2N)c(C(C)C)cn1 ; "1.5 H2O"]

Compound A

· 1.5 H$_2$O sesquihydrate the crystalline form VII has an XRPD pattern comprising characteristic peaks at diffraction angles (2θ) of about 13.1±0.2°, 19.9±0.2° and 20.2±0.2°.

In a preferred embodiment, the crystalline form VII has an XRPD pattern comprising characteristic peaks at diffraction angles (2θ) of about 13.1±0.2°, 16.9±0.2°, 19.9±0.2°, 20.2±0.2°, 24.9±0.2° and 28.8±0.2°.

In a more preferred embodiment, the crystalline form VII has an XRPD pattern comprising characteristic peaks at diffraction angles (2θ) of about 9.4±0.2°, 10.8±0.2°, 13.1±0.2°, 15.4±0.2°, 16.9±0.2°, 18.8±0.2°, 19.9±0.2°, 20.2±0.2°, 22.2±0.2°, 23.2±0.2°, 24.9±0.2°, 26.4±0.2° and 28.8±0.2°.

In a more preferred embodiment, the crystalline form VII has an XRPD pattern comprising peaks at the following diffraction angles (2θ):

| Peak No. | 2θ (°) ± 0.2° | I % |
|---|---|---|
| 1 | 9.4° | 14.9 |
| 2 | 9.9° | 3.7 |
| 3 | 10.8° | 7.9 |
| 4 | 12.8° | 6.7 |
| 5 | 13.1° | 61.2 |
| 6 | 14.3° | 5.4 |
| 7 | 15.0° | 2.9 |
| 8 | 15.4° | 10.6 |
| 9 | 15.8° | 3.8 |
| 10 | 16.9° | 17.3 |
| 11 | 17.4° | 4.7 |
| 12 | 18.8° | 10.8 |
| 13 | 19.5° | 3.4 |
| 14 | 19.9° | 31.0 |
| 15 | 20.2° | 100 |
| 16 | 20.7° | 2.9 |
| 17 | 21.8° | 6.3 |
| 18 | 22.2° | 15.9 |
| 19 | 23.2° | 15.1 |
| 20 | 23.8° | 2.0 |
| 21 | 24.1° | 5.7 |
| 22 | 24.9° | 20.4 |
| 23 | 25.8° | 2.2 |
| 24 | 26.4° | 9.5 |
| 25 | 28.1° | 2.3 |
| 26 | 28.8° | 22.3 |
| 27 | 29.5° | 4.3 |
| 28 | 31.5° | 2.1 |
| 29 | 32.5° | 4.4 |
| 30 | 33.0° | 6.1 |
| 31 | 33.6° | 1.2 |
| 32 | 34.4° | 1.5 |
| 33 | 34.7° | 1.8 |
| 34 | 35.2° | 1.6 |
| 35 | 35.5° | 1.3 |
| 36 | 36.5° | 2.2 |
| 37 | 37.8° | 1.2 |
| 38 | 38.2° | 1.6 |
| 39 | 38.5° | 1.4 |

Figure 14:
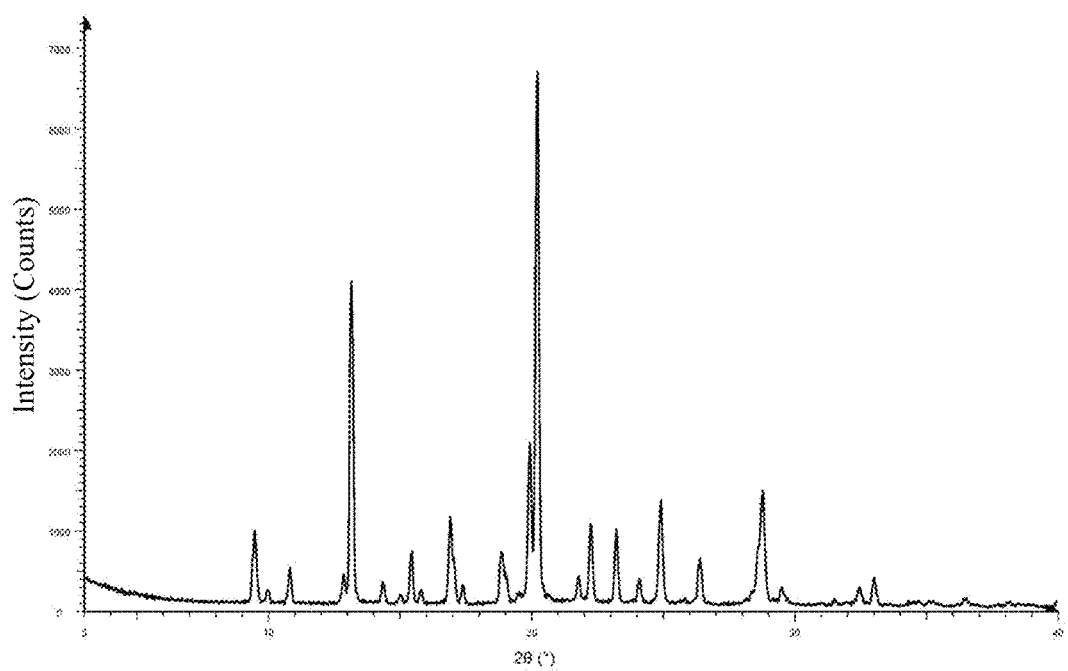
FIG. 14 is an X-ray powder diffraction pattern of crystalline form VII of compound A sesquihydrate.

In a more preferred embodiment, the crystalline form VII has an XRPD pattern comprising peaks at diffraction angles (2θ) essentially the same as shown in FIG. 14. In the most preferred embodiment, the XRPD peak positions of crystalline form VII are essentially the same as shown in FIG. 14.

In a more preferred embodiment, the crystalline form VII has a DSC graph comprising an endothermic peak at about 54.8° C. and endothermic/exothermic peaks at about 245/255° C.

In a more preferred embodiment, in a thermogravimetric analysis, the crystalline form VII has a weight loss of about 9.5% when heated to about 75° C.

Figure 15:
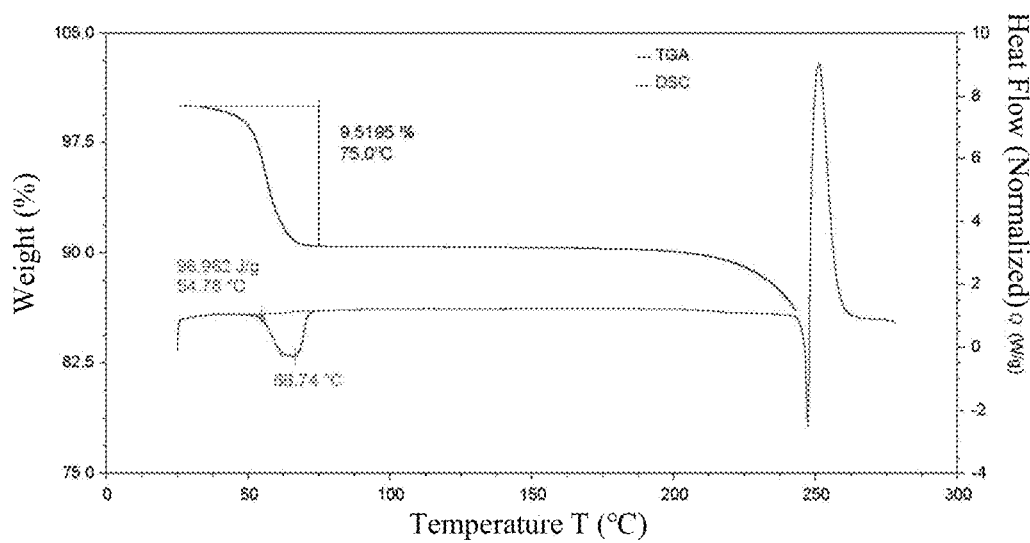
FIG. 15 is a differential scanning calorimetry (DSC) graph and a thermogravimetric analysis (TGA) graph of crystalline form VII of compound A sesquihydrate.

In a more preferred embodiment, the crystalline form VII has a DSC-TGA graph comprising characteristic peaks essentially the same as shown in FIG. 15. In the most preferred embodiment, the crystalline form VII has a DSC-TGA graph essentially the same as shown in FIG. 15.

In some preferred embodiments, the present invention provides a method for preparing crystalline form VII, comprising stirring compound A in a mixed solvent of an alcohol solvent (e.g., an alcohol having 1-6 carbon atoms, including but not limited to methanol, ethanol, 1-propanol, 2-propanol (isopropanol), 1-butanol, 2-butanol and tert-butanol) and water under heating (e.g., heating to 30-60° C., preferably 50° C.), to obtain a solution (the mixture may be filtered as needed to provide a solution), cooling the solution (e.g., cooling to 0-10° C., preferably 5° C.) to allow the precipitation of a solid, and filtering to obtain the crystalline form.

In some preferred embodiments, the volume ratio of the alcohol solvent to water is about 5:1 to 0.5:1, preferably about 3:1 to 1:1.

In some preferred embodiments, the weight/volume ratio (g/mL) of compound A to the mixed solvent is about 1:(20-80), preferably about 1:50.

In another embodiment, the present invention provides crystalline form VIII of compound A hemihydrate:

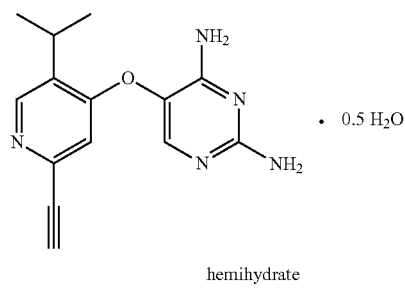

Compound A

· 0.5 H₂O hemihydrate the crystalline form VIII has an XRPD pattern comprising characteristic peaks at diffraction angles (2θ) of about 13.0±0.2°, 16.8±0.2°, 19.4±0.2°, 21.7±0.2°, 22.9±0.2° and 27.4±0.2°.

In a preferred embodiment, the crystalline form VIII has an XRPD pattern comprising characteristic peaks at diffraction angles (2θ) of about 10.3±0.2°, 13.0±0.2°, 16.8±0.2°, 19.1±0.2°, 19.4±0.2°, 21.1±0.2°, 21.7±0.2°, 22.9±0.2°, 25.8±0.2° and 27.4±0.2°.

In a more preferred embodiment, the crystalline form VIII has an XRPD pattern comprising characteristic peaks at diffraction angles (2θ) of about 8.7±0.2°, 10.3±0.2°, 10.8±0.2°, 13.0±0.2°, 14.1±0.2°, 14.8±0.2°, 16.8±0.2°, 17.5±0.2°, 19.1±0.2°, 19.4±0.2°, 21.1±0.2°, 21.7±0.2°, 22.3±0.2°, 22.9±0.2°, 25.8±0.2°, 27.4±0.2°, 27.8±0.2°, 30.4±0.2° and 31.6±0.2°.

In a more preferred embodiment, the crystalline form VIII has an XRPD pattern comprising peaks at the following diffraction angles (2θ):

| Peak No. | 2θ (°) ± 0.2° | I % |
|---|---|---|
| 1 | 8.7° | 21.7 |
| 2 | 10.3° | 47.6 |
| 3 | 10.8° | 16.5 |
| 4 | 12.2° | 12.2 |
| 5 | 13.0° | 50.1 |
| 6 | 14.1° | 13.9 |
| 7 | 14.8° | 19.7 |
| 8 | 15.5° | 7.7 |
| 9 | 16.4° | 20.3 |
| 10 | 16.8° | 72.4 |
| 11 | 17.5° | 17.7 |
| 12 | 19.1° | 30.0 |
| 13 | 19.4° | 88.1 |
| 14 | 20.7° | 16.3 |
| 15 | 21.1° | 24.4 |
| 16 | 21.7° | 100 |
| 17 | 22.3° | 19.5 |
| 18 | 22.9° | 56.4 |
| 19 | 23.8° | 11.9 |
| 20 | 24.1° | 14.3 |
| 21 | 24.5° | 13.5 |
| 22 | 25.0° | 11.4 |
| 23 | 25.3° | 11.1 |
| 24 | 25.8° | 25.3 |
| 25 | 26.3° | 12.0 |
| 26 | 27.4° | 94.8 |
| 27 | 27.8° | 22.3 |
| 28 | 30.4° | 13.7 |
| 29 | 31.6° | 14.2 |

-continued

| Peak No. | 2θ (°) ± 0.2° | I % |
|---|---|---|
| 30 | 32.0° | 10.8 |
| 31 | 32.8° | 7.7 |
| 32 | 33.5° | 8.7 |
| 33 | 33.9° | 7.5 |
| 34 | 34.3° | 6.8 |
| 35 | 35.3° | 9.9 |
| 36 | 35.9° | 10.0 |
| 37 | 36.5° | 6.3 |
| 38 | 37.4° | 6.4 |
| 39 | 37.9° | 5.9 |

Figure 16:
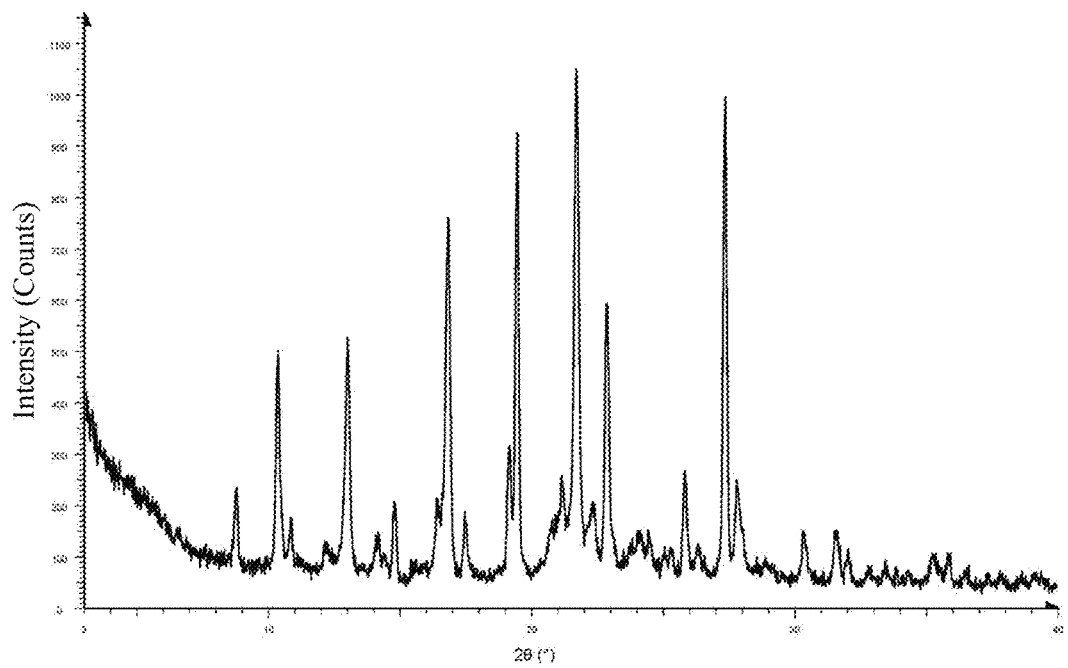
FIG. 16 is an X-ray powder diffraction pattern of crystalline form VIII of compound A hemihydrate.

In a more preferred embodiment, the crystalline form VIII has an XRPD pattern comprising peaks at diffraction angles (2θ) essentially the same as shown in FIG. 16. In the most preferred embodiment, the XRPD peak positions of crystalline form VIII are essentially the same as shown in FIG. 16.

In a more preferred embodiment, the crystalline form VIII has a DSC graph comprising an endothermic peak at about 50.9° C., an endothermic peak at about 79.1° C., an endothermic peak at about 124.9° C., and endothermic/exothermic peaks at about 245/255° C.

In a more preferred embodiment, in a thermogravimetric analysis, the crystalline form VIII has a weight loss of about 3.6% when heated to about 105° C.

Figure 17:
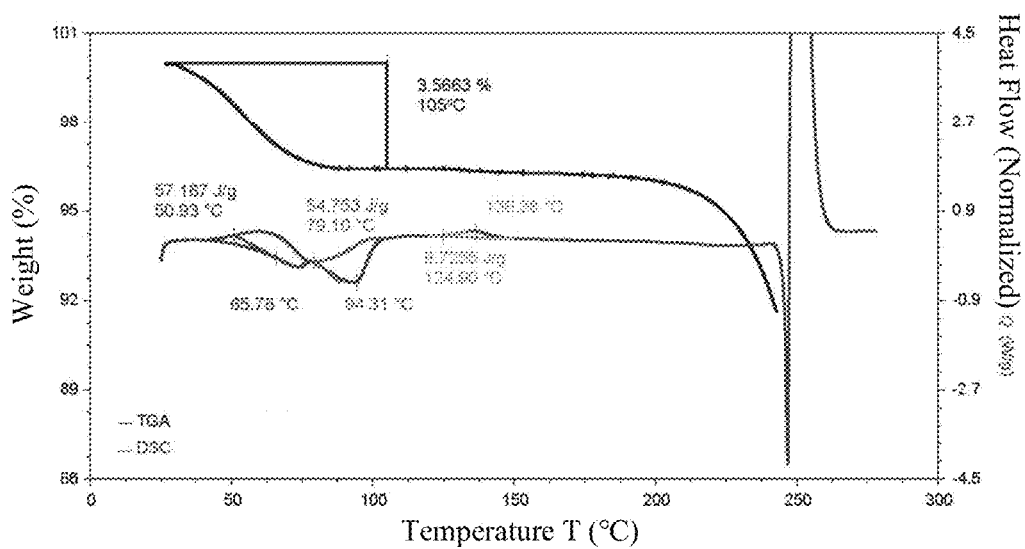
FIG. 17 is a differential scanning calorimetry (DSC) graph and a thermogravimetric analysis (TGA) graph of crystalline form VIII of compound A hemihydrate.

In a more preferred embodiment, the crystalline form VIII has a DSC-TGA graph comprising characteristic peaks essentially the same as shown in FIG. 17. In the most preferred embodiment, the crystalline form VIII has a DSC-TGA graph essentially the same as shown in FIG. 17.

In some preferred embodiments, the present invention provides a method for preparing crystalline form VIII, comprising stirring compound A in a mixed solvent of a ketone solvent (e.g., a ketone having 3-6 carbon atoms, including but not limited to acetone, butanone, methyl ethyl ketone, methyl isobutyl ketone and diethyl ketone) and water under heating (e.g., heating to 30-60° C., preferably 50° C.), to obtain a solution (the mixture may be filtered as needed to provide a solution), cooling the solution (e.g., cooling to 0-10° C., preferably 5° C.) to allow the precipitation of a solid, and filtering to obtain the crystalline form.

In some preferred embodiments, the volume ratio of the alcohol solvent to water is about 5:1 to 0.5:1, preferably about 3:1 to 1:1.

In some preferred embodiments, the weight/volume ratio (g/mL) of compound A to the mixed solvent is about 1:(20-80), preferably about 1:50.

Pharmaceutical Composition, Therapeutic Method and Use Thereof

In another embodiment, the present invention provides a pharmaceutical composition comprising any one or more of crystalline forms I, II, III, IV, V, VI, VII or VIII of the present invention and one or more pharmaceutically acceptable carriers.

In another embodiment, the present invention provides use of crystalline form I, II, III, IV, V, VI, VII or VIII of the present invention in the manufacture of a medicament for the prevention or treatment of a disease mediated by a P2X3 and/or P2X2/3 receptor antagonist.

In another embodiment, the present invention provides crystalline form I, II, III, IV, V, VI, VII or VIII of the present invention for use in the prevention or treatment of a disease mediated by a P2X3 and/or P2X2/3 receptor antagonist.

In another embodiment, the present invention provides a method for the prevention or treatment of a disease mediated by a P2X3 and/or P2X2/3 receptor antagonist, comprising administering to a subject in need thereof, preferably a mammal, a prophylactically or therapeutically effective amount of any one or more of crystalline forms I, II, III, IV, V, VI, VII or VIII of the present invention.

In a preferred embodiment, the disease mediated by a P2X3 and/or P2X2/3 receptor antagonist is selected from the group consisting of a urinary tract disease selected from reduced bladder capacity, frequent micturition, urge incontinence, stress incontinence, bladder hyperreactivity, benign prostatic hypertrophy, prostatitis, detrusor hyperreflexia, nocturia, urinary urgency, pelvic hypersensitivity, urethritis, pelvic pain syndrome, prostatodynia, cystitis, and idiopathic bladder hypersensitivity; a pain disease selected from inflammatory pain, surgical pain, visceral pain, dental pain, premenstrual pain, central pain, pain due to burns, migraine and cluster headaches, nerve injury, neuritis, neuralgia, poisoning, ischemic injury, interstitial cystitis, cancer pain, viral, parasitic or bacterial infection, post-traumatic injury and pain associated with irritable bowel syndrome; a cardiovascular system disease, preferably hypertension; a respiratory disease selected from chronic obstructive pulmonary disease, asthma and bronchospasm; a gastrointestinal disease selected from irritable bowel syndrome (preferably diarrhea-dominant irritable bowel syndrome), inflammatory bowel disease, biliary colic, renal colic, and pain associated with gastrointestinal distension.

As used herein, the term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g., Remington's Pharmaceutical Sciences (1990).

The composition of the present invention can act systemically and/or topically. To this end, it can be administered through a suitable route, such as through injection, intravenous, intraarterial, subcutaneous, intraperitoneal, intramuscular, or transdermal administration, or administered via oral, buccal, nasal, transmucosal, topical, as an ophthalmic formulation, or via inhalation.

For these routes of administration, the composition of the present invention can be administered in a suitable dosage form.

The dosage form may be solid, semi-solid, liquid, or gas formulations, specifically including, but not limited to, tablets, capsules, powders, granules, lozenges, hard candies, powders, sprays, creams, salves, suppositories, gels, pastes, lotions, ointments, aqueous suspensions, injectable solutions, suspensions, elixirs, and syrups.

The pharmaceutical composition of the present invention may be manufactured by any process well known in the art, e.g., by means of mixing, dissolving, granulating, drageemaking, levigating, emulsifying, lyophilizing processes, or the like.

As used herein, the term "therapeutically effective amount" refers to the amount of a compound being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, and 25 mg, etc.

Unless otherwise indicated, the term "treating" or "treatment", as used herein, means reversing, alleviating, inhibiting the progress of, or preventing a disorder, condition, or disease to which such term applies, or one or more symptoms of such disorder, condition, or disease.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e g, birds, amphibians, reptiles) and mammals, such as non-human primates, livestock and/or domesticated animals (such as sheep, dog, cat, cow, pig and the like).

The Advantageous Effects of the Crystalline Form of the Present Invention

1) The preferred crystalline forms of the present invention have good stability, and the color and properties thereof remain unchanged after being stored for a long period of time (e.g., 180 days of storage) at ambient temperature. In addition, the preferred crystalline forms of the present invention also have good stability under high temperature or high humidity conditions. For example, after crystalline form I was stored under a high temperature condition (such as 60° C.) for 30 days, its crystalline form did not change.
2) The preferred crystalline forms of the present invention have good fluidity, is easy to pulverize, and is feasible for preparing a pharmaceutical composition.
3) The preparation methods of the preferred crystalline forms of the present invention are simple and easy to implement, and the reaction conditions are mild. In addition, no multiple purifications are necessary, and the procedures are safe and environmentally friendly, which would facilitate the industrial production of the crystalline forms.

EXAMPLE

The present invention is explained in more detail below with reference to the examples, which are only used to illustrate the technical solutions of the present invention, and are not intended to limit the scope thereof. Those skilled in the art may make some non-essential improvements and adjustments, which still fall within the scope of the present invention.

Unless otherwise specified, the starting materials and reagents employed in the following Examples are all commercially available products or can be prepared through known methods.

The detection instruments and conditions used in the following examples are as follows:

(1) X-Ray Powder Diffraction (XRPD)

Instrument Model: Bruker D8 advance, equipped with a LynxEye detector

Test conditions: the anode target material was copper, the light pipe was set to (40 KV 40 mA), the 2θ scan angle for the sample was from 3° to 40°, and scan step was 0.02°.

(2) Differential Scanning Calorimetry Analysis (DSC)

Instrument Model: TA Discovery DSC 250 (TA Instruments, US)

Test conditions: the heating rate was 10° C./min, and dry nitrogen was used as the purge gas.

(3) Thermogravimetric Analysis (TGA)

Instrument Model: Discovery TGA 55 (TA Instruments, US)

Test conditions: automatic weighing in the heating furnace, the heating rate was 10° C./min, and dry nitrogen was used as the purge gas.

(4) Polarizing Microscope Analysis (PLM)

Instrument Model: Polarizing Microscope ECLIPSE LV100POL (Nikon, JPN)

Example 1: preparation of 5-((2-ethynyl-5-isopropylpyridin-4-yl)oxy)pyrimidine-2,4-diamine (Compound A) (see PCT/CN2018/112829, which is Incorporated Herein by Reference in its Entirety)

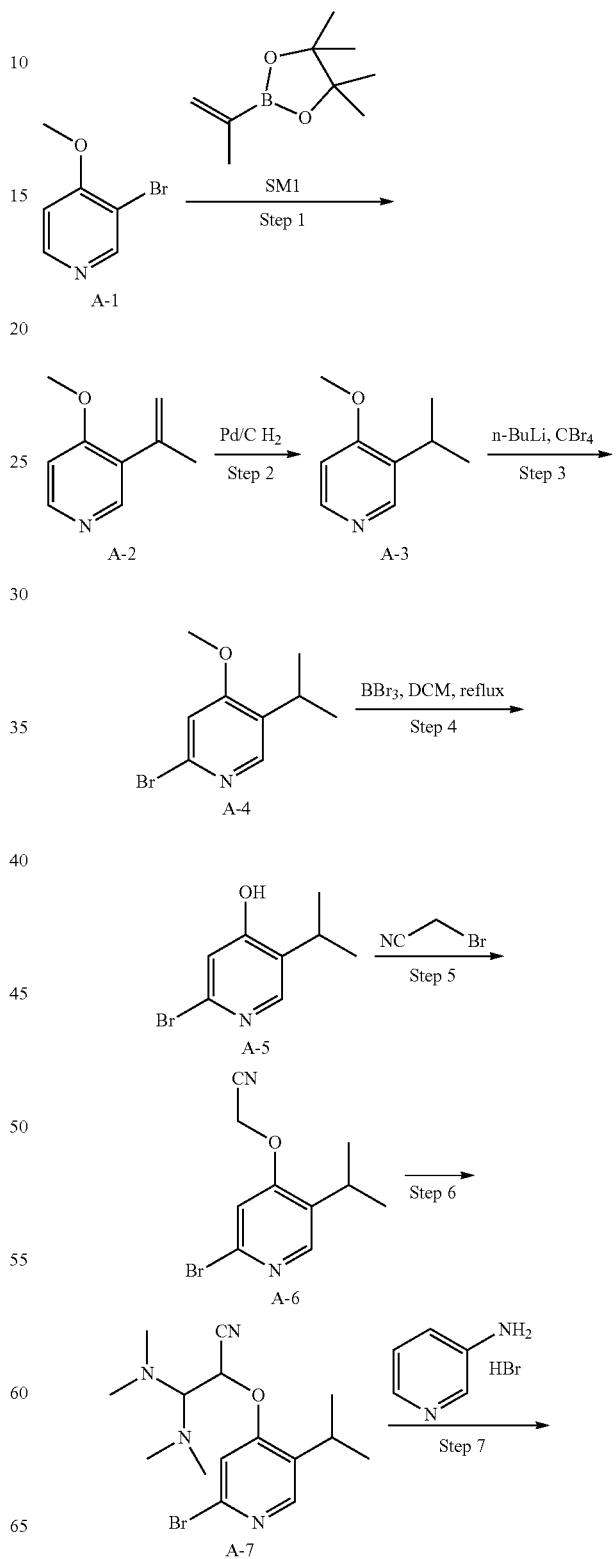

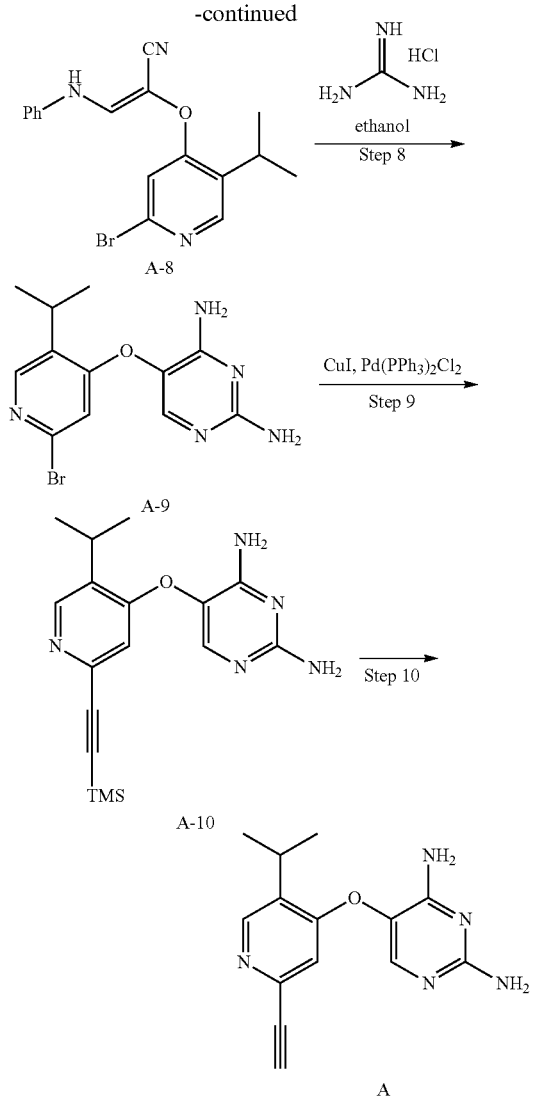

Step 1:

Compound A-1 (100 g, 0.54 mol) was dissolved in 1,4-dioxane (700 mL), the starting material SM1 (136 g, 0.81 mol), $K_2CO_3$ (149 g, 1.08 mol) and $Pd(PPh_3)_4$ (6.2 g, 5.4 mmol) were sequentially added, followed by addition of purified water (35 mL), and purge with nitrogen was performed for 3 times. Under the protection of nitrogen, the reaction was performed at 100° C. for 18 hours. LC-MS indicated the reaction of the starting materials was substantially complete. The reaction solution was cooled to room temperature, filtered, and the filter cake was washed with 1,4-dioxane (200 mL). The filtrate was concentrated under reduced pressure to remove 1,4-dioxane, followed by addition of purified water (200 mL), and extraction with ethyl acetate (400 mL×3). The organic phases were combined, dried over anhydrous sodium sulfate (100 g) for 30 min, filtered, and concentrated under reduced pressure to afford a crude product. The crude product was purified by column chromatography on silica gel (petroleum ether:ethyl acetate=20:1~10:1), to afford compound A-2 (79 g, yellow oil, yield: 99.75%).

$^1$H NMR (400 MHz, DMSO-$d_6$) δ 8.37 (d, J=5.6 Hz, 1H), 8.22 (s, 1H), 7.04 (d, J=5.6 Hz, 1H), 5.18 (s, 1H), 5.09 (s, 1H), 3.85 (s, 3H), 2.05 (s, 3H); MS m/z (ESI): 150.0 [M+H]$^+$.

Step 2:

Compound A-2 (79 g, 0.53 mol) was dissolved in anhydrous methanol (700 mL), 10% palladium/carbon (16 g) was added, and the reaction was performed under hydrogen (0.4 MPa) at room temperature for 18 hours. LC-MS indicated a small amount of the starting material remained. palladium/carbon (4 g) was supplemented, and the reaction was continued under hydrogen (0.4 MPa) at room temperature for 18 hours. LC-MS indicated the reaction of the starting materials was complete. The reaction solution was filtered, the filter cake was washed with methanol (100 mL), and the filtrate was concentrated under reduced pressure to give a crude product, compound A-3 (80 g, orange oily liquid, yield: 99.96%).

$^1$H NMR (400 MHz, DMSO-$d_6$) δ 8.31 (d, J=5.6 Hz, 1H), 8.28 (s, 1H), 6.98 (d, J=5.6 Hz, 1H), 3.86 (s, 3H), 3.21-3.09 (m, 1H), 1.21 (d, J=7.2 Hz, 6H); MS m/z (ESI): 152.1 [M+H]$^+$.

Step 3:

Compound N,N-dimethylethanolamine (46.3 g, 0.52 mol) was dissolved in n-hexane (400 mL). Under the protection of nitrogen, the reaction was cooled to −15° C.~−20° C., 2.4 M/L n-butyl lithium (434 mL, 1.04 mol) was slowly dropwise added. After the dropwise addition was complete, the reaction was kept at the temperature for 30 minutes, and then a solution of compound A-3 (40 g, 0.26 mol) in toluene (200 mL) was slowly dropwise added at −15° C.~−20° C. After the dropwise addition was complete, the reaction was kept at the temperature for 30 minutes. The reaction solution was cooled to −70° C., a solution of carbon tetrabromide (172.4 g, 0.52 mol) in toluene (500 mL) was slowly dropwise added, and the temperature was controlled at −70° C.~−75° C. After the dropwise addition was complete, the reaction was kept at the temperature for 1 hour. LC-MS indicated the reaction of the starting materials was complete. The reaction was quenched by adding water (500 mL), and extracted with ethyl acetate (500 mL×3). The organic phases were combined, washed once with saturated brine (500 mL), dried over anhydrous sodium sulfate (400 g) for half an hour, filtered and concentrated. The crude product was isolated by column chromatography on silica gel (petroleum ether:ethyl acetate=200:1~50:1) to afford compound A-4 (25 g, light yellow oily liquid, yield: 41.81%).

$^1$H NMR (400 MHz, DMSO-$d_6$) δ 8.06 (s, 1H), 7.20 (s, 1H), 3.89 (s, 3H), 3.13-3.05 (m, 1H), 1.18 (d, J=6.8 Hz, 6H); MS m/z (ESI): 229.9 [M+H]$^+$.

Step 4:

Compound A-4 (25 g, 0.11 mol) was dissolved in dichloromethane (300 mL). Under the protection of nitrogen, the reaction was cooled to 0° C.~−5° C., and a solution of boron tribromide (140.3 g, 0.55 mol) was slowly added. After competition of the addition, the reaction solution was warmed to reflux, and the reaction was performed for 18 hours. LC-MS indicated the reaction of the starting materials was complete. The reaction solution was cooled to room temperature, and slowly dropwise added to 500 g ice. After the dropwise addition was complete, a saturated solution of sodium bicarbonate was dropwise added to adjust pH to 7~8. The reaction was filtered, the filter cake was washed thrice with ethyl acetate (400 mL), the filtrate was separated, and the aqueous phase was extracted with ethyl acetate (400 mL×3) again. All the organic phases were combined, dried over anhydrous sodium sulfate (500 g) for half an hour, filtered, and the filtrate was concentrated under reduced pressure to afford compound A-5 (20 g, light yellow solid, yield: 84.17%).

$^1$H NMR (400 MHz, DMSO-d$_6$) δ 11.11 (s, 1H), 7.99 (s, 1H), 6.90 (s, 1H), 3.10-3.02 (m, 1H), 1.18 (d, J=6.8 Hz, 6H); MS m/z (ESI): 215.9 [M+H]$^+$.

Step 5:

Compound A-5 (10 g, 0.047 mol) was dissolved in DMF (50 mL). Under the protection of nitrogen, potassium carbonate (12.8 g, 0.093 mol) and bromoacetonitrile (8.4 g, 0.07 mol) were sequentially added, and the reaction was stirred at room temperature for 2 hours. LC-MS indicated the reaction of the starting materials was complete. The reaction was quenched by adding water (50 mL), and extracted with ethyl acetate (50 mL×4). The combined organic phases were washed with saturated brine (50 mL×3), added with anhydrous sodium sulfate, dried for half an hour, and filtered. The filtrate was concentrated under reduced pressure, and the crude product was isolated by column chromatography on silica gel (petroleum ether:ethyl acetate=20:1~5:1) to afford compound A-6 (4 g, light yellow solid, yield: 33.38%).

$^1$H NMR (400 MHz, DMSO-d$_6$) δ 8.18 (s, 1H), 7.40 (s, 1H), 5.37 (s, 2H), 3.14-3.06 (m, 1H), 1.21 (d, J=6.8 Hz, 6H); MS m/z (ESI): 254.8 [M+H]$^+$.

Step 6:

Compound A-6 (4 g, 0.016 mol) was dissolved in DMF (50 mL). Under the protection of nitrogen, tert-butoxy bis(dimethylamino)methane (8.2 g, 0.048 mol) was added, the reaction was heated to 100° C., and stirred for 2 hours. LC-MS indicated the reaction of the starting materials was complete. The reaction solution was cooled to room temperature, quenched by adding water (50 mL), and then extracted with ethyl acetate (50 mL×3). The organic phase was then washed with saturated brine (50 mL×3), added with anhydrous sodium sulfate, dried for half an hour, and filtered. The filtrate was concentrated under reduced pressure, and the crude product was isolated by column chromatography on silica gel (petroleum ether:ethyl acetate=10: 1~5:1) to afford compound A-7 (3.8 g, light yellow solid, yield: 66.90%). MS m/z (ESI): 309.7 [M−45+H]$^+$.

Step 7:

Compound A-7 (3.54 g, 0.01 mol) was dissolved in DMF (25 mL). Under the protection of nitrogen, aniline hydrobromide (2.08 g, 0.012 mol) was added, the reaction was heated to 100° C., and stirred for 2 hours. LC-MS indicated the reaction of the starting materials was complete. The reaction solution was cooled to room temperature, quenched by adding water (25 mL), and extracted with ethyl acetate (20 mL×3). The organic phase was then washed with saturated brine (20 mL×3), added with anhydrous sodium sulfate, dried for half an hour, and filtered. The filtrate was concentrated under reduced pressure, and the crude product was isolated by column chromatography on silica gel (petroleum ether:ethyl acetate=20:1~5:1) to afford compound A-8 (3.1 g, light yellow solid, yield: 86.59%).

$^1$H NMR (400 MHz, DMSO-d$_6$) δ 9.36 (d, J=12.8 Hz, 1H), 8.28 (s, 1H), 7.95 (d, J=12.8 Hz, 1H), 7.32-7.24 (m, 4H), 7.20 (s, 1H), 6.99 (t, J=7.2 Hz, 1H), 3.31-3.26 (m, 1H), 1.28 (d, J=6.8 Hz, 6H); MS m/z (ESI): 357.7 [M+H]$^+$.

Step 8:

Guanidine hydrochloride (2.4 g, 25.2 mmol) was added to anhydrous ethanol (50 mL). Under the protection of nitrogen, sodium methoxide (2.4 g, 25.2 mmol) was added, the reaction was stirred at room temperature for half an hour, followed by addition of compound A-8 (3 g, 8.4 mmol). After completetion of the addition, the reaction solution was heated to reflux, and the reaction was performed for 18 hours. LC-MS indicated the reaction of the starting materials was complete. The reaction solution was cooled to room temperature, filtered, the filtrate was concentrated under reduced pressure, and the crude product was isolated by column chromatography on silica gel (DCM:MeOH=50: 1~20:1) to afford compound A-9 (900 mg, light yellow solid, yield: 33.17%, compound 2).

$^1$H NMR (400 MHz, DMSO-d$_6$) δ 8.19 (s, 1H), 7.62 (s, 1H), 6.56 (s, 1H), 6.47 (s, 2H), 6.06 (s, 2H), 3.32-3.27 (m, 1H), 1.28 (d, J=6.8 Hz, 6H); MS m/z (ESI): 323.7 [M+H]$^+$.

Step 9:

Compound A-9 (3 g, 9.29 mmol) was dissolved in 1,4-dioxane (40 mL), trimethylsilylacetylene (9 g, 92.9 mmol), DIEA (12 g, 92.9 mmol), CuI (0.6 g) and Pd(PPh$_3$)$_2$Cl$_2$ (0.6 g) were sequentially added, and purge with nitrogen was performed for 3 times. Under the protection of nitrogen, the reaction was performed at 50° C. for 2 hours. LC-MS indicated the reaction of the starting materials was substantially complete. The reaction solution was cooled to room temperature, filtered, the filter cake was washed with 1,4-dioxane (10 mL), the filtrate was concentrated under reduced pressure to remove dioxane, followed by addition of purified water (100 mL), and extraction with ethyl acetate (100 mL×3). The organic phases were combined, added with anhydrous sodium sulfate (20 g), dried for 30 min, filtered, and concentrated under reduced pressure to afford a crude product, which was purified by column chromatography on silica gel (petroleum ether:ethyl acetate=20:1~5:1) to afford compound A-10 (2 g, yield 63.1%). MS m/z (ESI): 341.9 [M+H]$^+$.

Step 10:

Compound A-10 (2 g, 5.87 mmol) was dissolved in THF (20 mL), and TBAF (1.53 g, 5.87 mmol) was added. The reaction was performed at room temperature for 10 minutes. LC-MS indicated the reaction of the starting materials was complete. The reaction solution was rotary evaporated to dryness to give an oily residue. The residue was purified by column chromatography on silica gel (petroleum ether:ethyl acetate=1:3) to afford compound A (0.7 g, yellow solid, yield 44.6%).

$^1$H NMR (300 MHz, DMSO-d$_6$) δ 8.33 (s, 1H), 7.56 (s, 1H), 6.50 (s, 1H), 6.41 (s, 2H), 6.01 (s, 2H), 4.20 (s, 1H), 3.37-3.31 (m, 1H), 1.28 (d, J=6.8 Hz, 6H). MS m/z (ESI): 269.8 [M+H]$^+$.

Example 2: Preparation of Crystalline Form I of Compound A Anhydrate (Method One)

10.0 g of compound A was added to 100 mL of water, 6M hydrochloric acid was added dropwise at 0° C. until the solid was completely dissolved, and the mixture was stirred at room temperature for 1 h. After the solution was filtered, the filtrate was collected, and dropwise added with a 1M NaOH aqueous solution at 0° C. until the pH was 12, and a white solid precipitated. The solid was collected after filtration. The obtained solid was stirred in 100 mL of water for 2 h, and the solid was collected by filtration. The solid was vacuum dried at 50° C. for 6 hours, and the obtained solid was the target crystalline form. The XRPD pattern obtained by X-ray powder diffraction detection is shown in FIG. 1; the DSC and TGA graph obtained by a DSC and TGA analysis is shown in FIG. 2; and the sample was observed under a scanning electron microscope, and the crystal morphology is shown in FIG. 3.

The thermogravimetric analysis (TGA) showed that the crystalline form sample had a weight loss of 0.1% between 25-150° C., indicating that this crystalline form does not contain crystal water.

Example 3: Preparation of Crystalline Form I of Compound A Anhydrate (Method Two)

1.3 g of compound A was added to 100 mL of tetrahydrofuran and stirred at room temperature until complete dissolution, the resulting solution was filtered, and the filtrate was collected. 300 ml of n-heptane was slowly added dropwise to the filtrate, and the mixture was stirred overnight at room temperature to allow the precipitation of a solid, and the suspension was filtered to obtain a crystalline form. The XRPD pattern obtained by X-ray powder diffraction detection is the same as that in FIG. 1.

Example 4: Preparation of Crystalline Form I of Compound A Anhydrate (Method Three)

2.0 g of compound A was added to 80 mL of tetrahydrofuran and stirred at 50° C. until complete dissolution, and was filtered while hot. The filtrate was cooled to 5° C., 100 ml of methyl tert-butyl ether was slowly added dropwise thereto, and the mixture was stirred at 5° C. for 30 min. A solid precipitated, and the suspension was filtered to obtain a crystalline form. The XRPD pattern obtained by X-ray powder diffraction detection is the same as that in FIG. 1.

Example 5: Preparation of Crystalline Form II of Compound A Monohydrate 2.0 g of compound A was suspended in 100 mL of methanol (containing 1 wt. % water) and stirred at room temperature for 3 days, and the solid was collected by filtration. The XRPD pattern obtained by X-ray powder diffraction detection is shown in FIG. 4; and the DSC and TGA graph obtained by a DSC and TGA analysis is shown in FIG. 5. The thermogravimetric analysis (TGA) showed that the crystalline form sample had a weight loss of 6.2% between 25-100° C., indicating that this crystalline form contains 1 molecule of crystal water, since the theoretical water content of a sample containing 1 molecule of crystal water is 6.27%.

Example 6: Preparation of Crystalline Form III of Compound A Hemihydrate 4.0 g of compound A was added to 50 mL of dimethyl sulfoxide, and stirred at room temperature until complete dissolution. The resulting solution was filtered, and the filtrate was collected. 100 ml of water was slowly added dropwise to the filtrate, the resulting mixture was stirred at room temperature overnight, and a solid precipitated. The suspension was filtered to obtain the crystalline form. The XRPD pattern obtained by X-ray powder diffraction detection is shown in FIG. 6; and the DSC and TGA graph obtained by a DSC and TGA analysis is shown in FIG. 7. The thermogravimetric analysis (TGA) showed that the crystalline form sample had a weight loss of 3.6% between 25-80° C., indicating that this crystalline form contains 0.5 molecule of crystal water, since the theoretical water content of a sample containing 0.5 molecule of crystal water is 3.24%.

Example 7: Preparation of Crystalline Form IV of Compound A Sesquihydrate (Method One)

2.0 g of compound A was suspended in 100 mL of water and stirred at room temperature for 3 days, and the solid was collected by filtration. The XRPD pattern obtained by X-ray powder diffraction detection is shown in FIG. 8; and the DSC and TGA graph obtained by a DSC and TGA analysis is shown in FIG. 9. The thermogravimetric analysis (TGA) showed that the crystalline form sample had a weight loss of 9.4% between 25-100° C., indicating that this crystalline form contains 1.5 molecules of crystal water, since the theoretical water content of a sample containing 1.5 molecules of crystal water is 9.12%.

Example 8: Preparation of Crystalline Form IV of Compound A Sesquihydrate (Method Two)

1.3 g of compound A was added to 100 mL of tetrahydrofuran, and stirred at room temperature until complete dissolution. The resulting solution was filtered, and the filtrate was collected. 300 ml of water was slowly added dropwise to the filtrate, and the mixture was stirred overnight at room temperature to allow the precipitation of a solid. The suspension was filtered to obtain the crystalline form. The XRPD pattern obtained by X-ray powder diffraction detection is the same as that in FIG. 8.

Example 9: Preparation of Crystalline Form V of Compound A Monohydrate 4.0 g of compound A was added to 50 mL of dimethyl sulfoxide and stirred at room temperature until complete dissolution, and the filtrate was collected after filtration. The filtrate was slowly dropwise added with 100 ml of methanol (containing 1 wt. % water), and stirred overnight at room temperature to allow the precipitation of a solid. The suspension was filtered to obtain a crystalline form. The XRPD pattern obtained by X-ray powder diffraction detection is shown in FIG. 10; and the DSC and TGA graph obtained by a DSC and TGA analysis is shown in FIG. 11. The thermogravimetric analysis (TGA) showed that the crystalline form sample had a weight loss of 6.8% between 25-80° C., indicating that this crystalline form contains 1 molecule of crystal water, since the theoretical water content of a sample containing 1 molecule of crystal water is 6.27%.

Example 10: Preparation of Crystalline Form VI of Compound A Monohydrate 5.0 g of compound A was added to 100 mL of a mixed solvent (4/1) of acetone and water to form a suspension, which was stirred at room temperature for 3 days, and the solid was collected by filtration. The XRPD pattern obtained by X-ray powder diffraction detection is shown in FIG. 12; and the DSC and TGA graph obtained by a DSC and TGA analysis is shown in FIG. 13.

The water content determined by employing a V20 Karl Fischer Moisture Titrator was 6.3%, indicating that this crystalline form contains 1 molecule of crystal water, since the theoretical water content of a sample containing 1 molecule of crystal water is 6.27%.

Example 11: Preparation of Crystalline Form VII of Compound A Sesquihydrate 2.0 g of compound A was added to 100 mL of a mixed solvent (1/1) of ethanol and water, stirred at 50° C. until complete dissolution, and filtered while hot. The filtrate was slowly cooled to 5° C., and the solid was collected by filtration. The XRPD pattern obtained by X-ray powder diffraction detection is shown in FIG. 14; and the DSC and TGA graph obtained by a DSC and TGA analysis is shown in FIG. 15. The thermogravimetric analysis (TGA) showed that the crystalline form sample had a weight loss of 9.5% between 25-75° C., indicating that this crystalline form contains 1.5 molecules of crystal water, since the theoretical water content of a sample containing 1.5 molecules of crystal water is 9.12%.

Example 12: Preparation of Crystalline Form VIII of Compound A Hemihydrate 2.0 g of compound A was added to 100 mL of a mixed solvent of acetone and water (1/1), stirred at 50° C. until complete dissolution, and filtered while hot. The filtrate was slowly cooled to 5° C., and the solid was collected by filtration. The XRPD pattern obtained by X-ray powder diffraction detection is shown in FIG. 16; and the DSC and TGA graph obtained by a DSC and TGA analysis is shown in FIG. 17. The thermogravimetric analysis (TGA) showed that the crystalline form sample had a weight loss of 3.6% between 25-105° C., indicating that this crystalline form contains 0.5 molecule of crystal water, since the theoretical water content of a sample containing 0.5 molecule of crystal water is 3.24%.

EXPERIMENTAL EXAMPLE

Experimental Example 1: Room Temperature Stability Test

Figure 18:
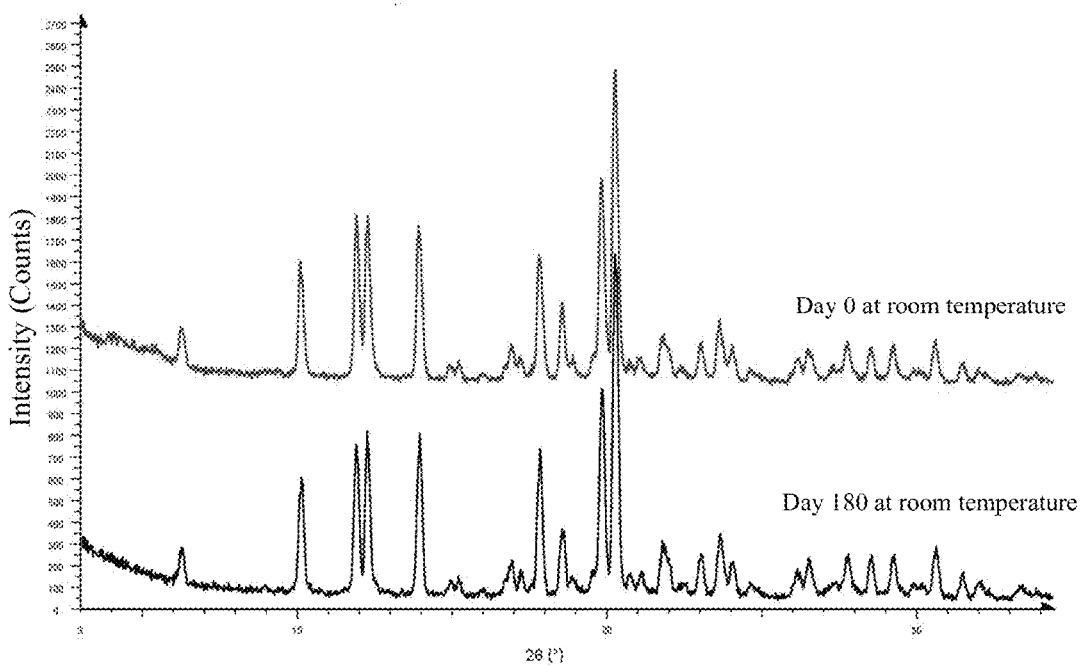
FIG. 18 is an XRPD pattern comparison of crystalline form I of compound A anhydrate before and after the room temperature stability test.

The crystalline form I prepared in Example 2, the crystalline form II prepared in Example 5, the crystalline form III prepared in Example 6, the crystalline form IV prepared in Example 7, the crystalline form V prepared in Example 9, the crystalline form VI prepared in Example 10, the crystalline form VII prepared in Example 11, and the crystalline form VIII prepared in Example 12 were respectively placed in a medicinal low-density polyethylene bag, sealed, and placed at room temperature for 180 days. The XRPD was measured with a Bruker D8 advance X-ray powder diffractometer. The results showed that the samples of crystalline forms I, II, III, IV, V, VI, VII and VIII had no change in the crystalline form after 180 days, and the stability was good. FIG. 18 shows the XRPD pattern comparison of crystalline form I before and after being placed at room temperature for 180 days.

Experimental Example 2: High Temperature Stability Test

Figure 19:
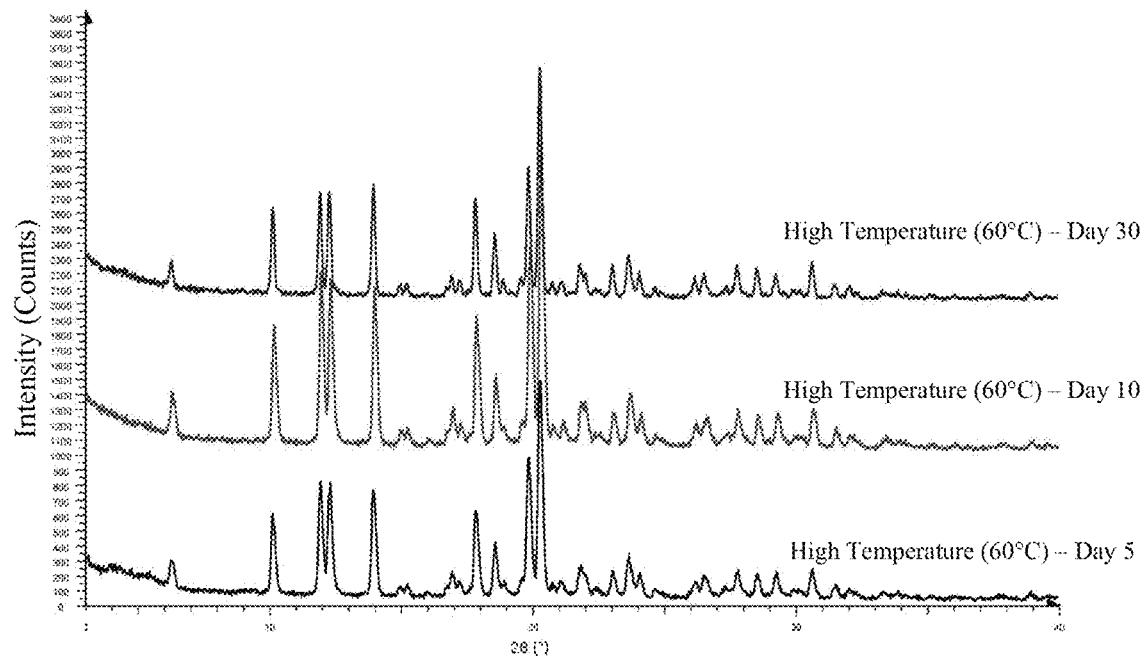
FIG. 19 is an XRPD pattern comparison of crystalline form I of compound A anhydrate before and after the high temperature stability test.

The stability of the crystalline form I prepared in Example 2 was investigated at 60° C., and the XRPD pattern was measured with a Bruker D8 advance X-ray powder diffractometer (see FIG. 19). The results showed that the crystalline form I sample had no change in the crystalline form after 5, 10 and 30 days, and the stability thereof is excellent.

Experimental Example 3: High Humidity Stability Test

Figure 20:
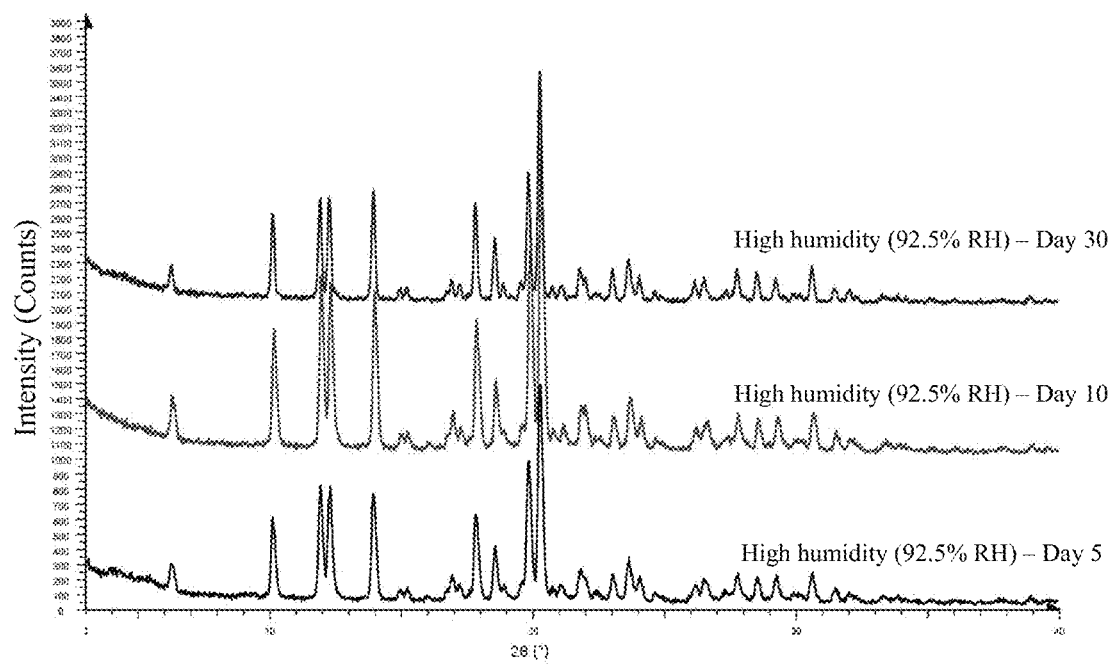
FIG. 20 is an XRPD pattern comparison of crystalline form I of compound A anhydrate before and after the high humidity stability test.

The stability of the crystalline form I prepared in Example 2 was investigated under a condition of 92.5% RH/25° C., and the XRPD pattern was measured with a Bruker D8 advance X-ray powder diffractometer (see FIG. 20). The results showed that the crystalline form I sample had no change in the crystalline form after 5, 10 and 30 days, and the stability thereof is excellent.

Experimental Example 4: Physical Grinding Stability Test

Figure 21:
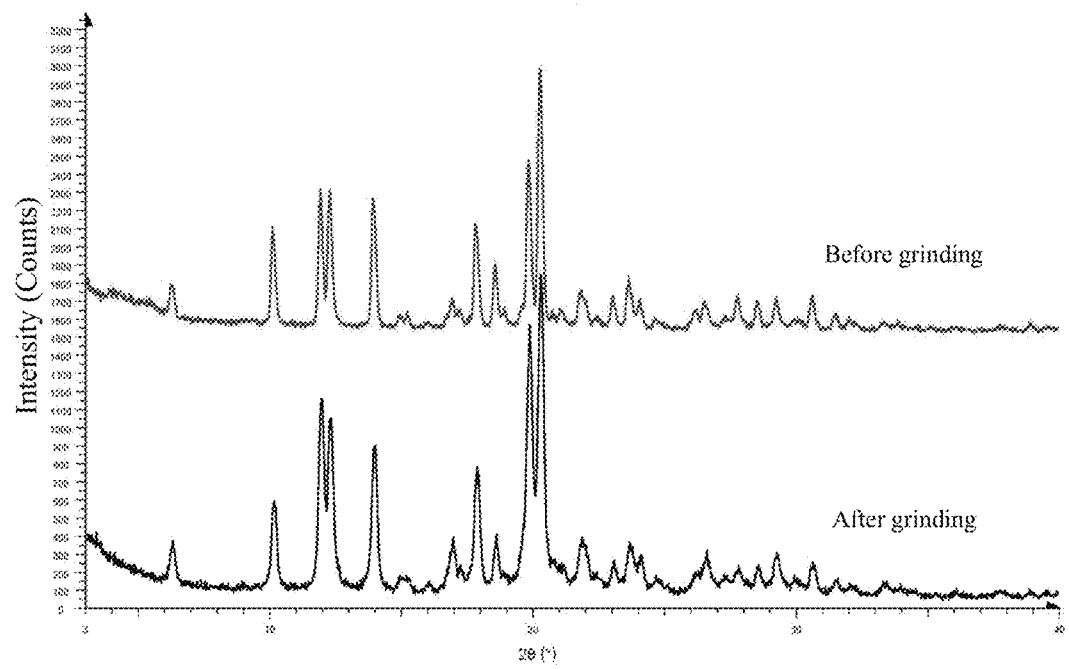
FIG. 21 is an XRPD pattern comparison of crystalline form I of compound A anhydrate before and after the physical grinding stability test.

The crystalline form I prepared in Example 2 was physically ground for 2 minutes, and then the XRPD pattern was measured with a Bruker D8 advance X-ray powder diffractometer (see FIG. 21). The results showed that the crystalline form I sample had no change in the crystalline form, and the stability thereof is excellent.

Various modifications to the invention in addition to those described herein will become apparent to those skilled in the art from the foregoing description. Such modifications are intended to fall within the scope of the appended claims Each reference, including all patents, applications, journal articles, books and any other disclosure, referred to herein is hereby incorporated by reference in its entirety.

What is claimed is:
1. A crystalline form I of compound A anhydrate:

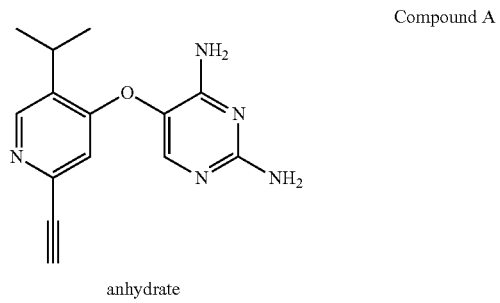 [SMILES: C#Cc1cc(Oc2cnc(N)nc2N)c(C(C)C)cn1]

Compound A anhydrate the crystalline form I has an X-Ray Powder Diffraction (XRPD) pattern comprising characteristic peaks at diffraction angles (2θ) of about 11.9±0.2°, 12.3±0.2°, 13.9±0.2°, 19.8±0.2° and 20.3±0.2°.

2. A method for preparing the crystalline form I of compound A anhydrate according to claim 1, comprising the following steps:
　1) adding compound A to water, followed by addition of an acid, stirring to dissolve compound A and obtain a solution, which is optionally filtered to obtain a filtrate;
　2) adding a base to the solution or filtrate obtained in step 1), and collecting the precipitated solid by filtration; and
　3) adding the obtained solid to water and stirring, filtering to collect the solid, which is optionally dried to obtain crystalline form I;
　alternatively, the method comprising dissolving compound A in a good solvent to form a solution, then adding an anti-solvent thereto, and stirring to allow the precipitation of a solid, which is filtered to obtain the crystalline form.

3. The method according to claim 2, wherein the acid is acetic acid, trifluoroacetic acid, hydrochloric acid or sulfuric acid.

4. The method according to claim 2, wherein the base is sodium hydroxide, potassium hydroxide or ammonia.

5. The method according to claim 2, wherein the good solvent is a cyclic ether having 3-10 carbon atoms; and/or the anti-solvent is a hydrocarbon having 5-10 carbon atoms or a linear ether having 2-6 carbon atoms.

6. The method according to claim 2, wherein the good solvent is tetrahydrofuran, 2-methyltetrahydrofuran or dioxane; and/or the anti-solvent is dichloromethane, trichloromethane, n-hexane, n-heptane, toluene, diethyl ether, diisopropyl ether or methyl tert-butyl ether.

7. The method according to claim 2, wherein the good solvent is tetrahydrofuran; and
the anti-solvent is n-heptane or methyl tert-butyl ether.

8. The method according to claim 2, wherein the weight/volume ratio (g/mL) of compound A to the good solvent is 1:(30-120).

9. The method according to claim 2, wherein the weight/volume ratio (g/mL) of compound A to the good solvent is 1:40 or 1:100.

10. The method according to claim 2, wherein the volume ratio of the good solvent to the anti-solvent is 1:1 to 1:5.

11. A pharmaceutical composition comprising the crystalline form I of compound A anhydrate according to claim 1, and one or more pharmaceutically acceptable carriers.

12. A method for the prevention or treatment of a disease mediated by a P2X3 and/or P2X2/3 receptor antagonist, comprising administering to a subject in need thereof the crystalline form I of compound A anhydrate according to claim 1.

13. The method according to claim 12, wherein the disease is selected from the group consisting of a urinary tract disease selected from reduced bladder capacity, frequent micturition, urge incontinence, stress incontinence, bladder hyperreactivity, benign prostatic hypertrophy, prostatitis, detrusor hyperreflexia, nocturia, urinary urgency, pelvic hypersensitivity, urethritis, pelvic pain syndrome, prostatodynia, cystitis, and idiopathic bladder hypersensitivity; a pain disease selected from inflammatory pain, surgical pain, visceral pain, dental pain, premenstrual pain, central pain, pain due to burns, migraine and cluster headaches, nerve injury, neuritis, neuralgia, poisoning, ischemic injury, interstitial cystitis, cancer pain, viral, parasitic or bacterial infection, post-traumatic injury and pain associated with irritable bowel syndrome; a cardiovascular system disease; a respiratory disease selected from chronic obstructive pulmonary disease, asthma and bronchospasm; a gastrointestinal disease selected from irritable bowel syndrome, inflammatory bowel disease, biliary colic, renal colic, and pain associated with gastrointestinal distension.

14. The method according to claim 13, wherein the cardiovascular system disease is hypertension; and the irritable bowel syndrome is diarrhea-dominant irritable bowel syndrome.

15. The crystalline form I of compound A anhydrate according to claim 1, wherein the crystalline form I has an XRPD pattern comprising characteristic peaks at diffraction angles (2θ) of about 10.1±0.2°, 11.9±0.2°, 12.3±0.2°, 13.9±0.2°, 17.8±0.2°, 18.6±0.2°, 19.8±0.2° and 20.3±0.2°.

16. The crystalline form I of compound A anhydrate according to claim 1, wherein the crystalline form I has an XRPD pattern comprising characteristic peaks at diffraction angles (2θ) of about 6.2±0.2°, 10.1±0.2°, 11.9±0.2°, 12.3±0.2°, 13.9±0.2°, 16.9±0.2°, 17.8±0.2°, 18.6±0.2°, 19.8±0.2°, 20.3±0.2°, 21.8±0.2°, 23.0±0.2°, 23.6±0.2°, 24.1±0.2°, 26.2±0.2°, 26.5±0.2°, 27.8±0.2°, 28.5±0.2°, 29.3±0.2° and 30.6±0.2°.

17. The crystalline form I of compound A anhydrate according to claim 1, wherein the crystalline form I has a DSC graph comprising endothermic/exothermic peaks at 245/255° C.

18. The crystalline form I of compound A anhydrate according to claim 1, wherein in a thermogravimetric analysis, the crystalline form I has a weight loss of 0.1% when heated to 100-150° C.

19. A crystalline form,
wherein the crystalline form is selected from the group consisting of:
a crystalline form II of compound A monohydrate:

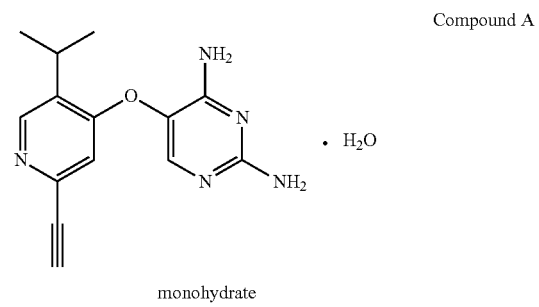 [SMILES: C#Cc1cc(Oc2cnc(N)nc2N)c(C(C)C)cn1 ; O]

monohydrate wherein the crystalline form II has an XRPD pattern comprising characteristic peaks at diffraction angles (2θ) of about 13.0±0.2°, 19.5±0.2°, 19.9±0.2° and 22.7±0.2°;
a crystalline form III of compound A hemihydrate:

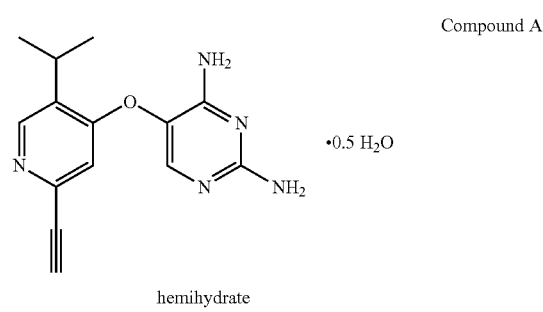 [SMILES: C#Cc1cc(Oc2cnc(N)nc2N)c(C(C)C)cn1 ; "·0.5 H2O"]

hemihydrate wherein the crystalline form III has an XRPD pattern comprising characteristic peaks at diffraction angles (2θ) of about 10.8±0.2°, 20.5±0.2° and 21.7±0.2°;
a crystalline form IV of compound A sesquihydrate:

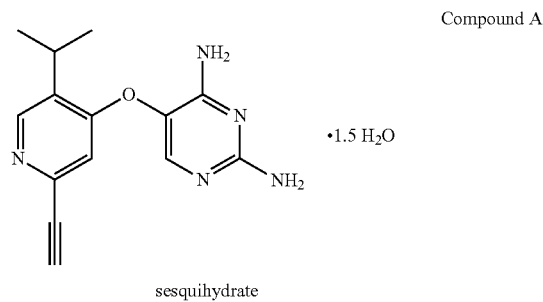 [SMILES: C#Cc1cc(Oc2cnc(N)nc2N)c(C(C)C)cn1 ; "·1.5 H2O"]

sesquihydrate wherein the crystalline form IV has an XRPD pattern comprising characteristic peaks at diffraction angles (2θ) of about 12.3±0.2°, 12.6±0.2°, 17.2±0.2°, 21.3±0.2°, 24.1±0.2° and 27.9±0.2°;

a crystalline form V of compound A monohydrate:

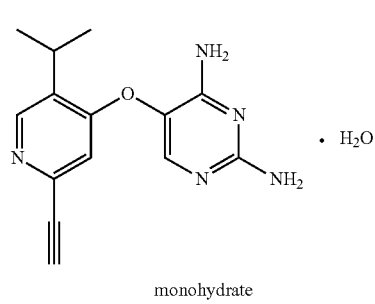

monohydrate wherein the crystalline form V has an XRPD pattern comprising characteristic peaks at diffraction angles (2θ) of about 14.1±0.2°, 21.0±0.2° and 29.6±0.2°;

a crystalline form VI of compound A monohydrate:

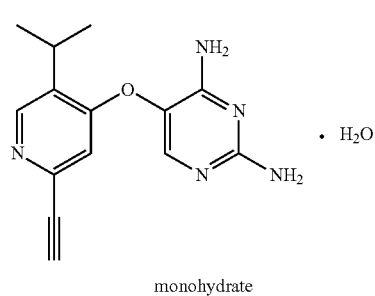

monohydrate wherein the crystalline form VI has an XRPD pattern comprising characteristic peaks at diffraction angles (2θ) of about 10.4±0.2°, 12.1±0.2°, 16.6±0.2°, 20.7±0.2°, 22.8±0.2° and 27.3±0.2°;

a crystalline form VII of compound A sesquihydrate:

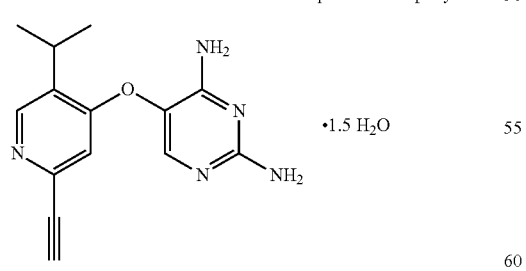

wherein the crystalline form VII has an XRPD pattern comprising characteristic peaks at diffraction angles (2θ) of about 13.1±0.2°, 19.9±0.2° and 20.2±0.2°; or a crystalline form VIII of compound A hemihydrate:

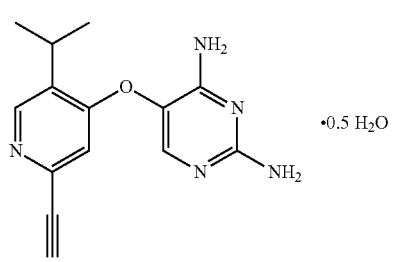 [SMILES: C#Cc1cc(Oc2cnc(N)nc2N)c(C(C)C)cn1 ; "·0.5 H2O"]

wherein the crystalline form VIII has an XRPD pattern comprising characteristic peaks at diffraction angles (2θ) of about 13.0±0.2°, 16.8±0.2°, 19.4±0.2°, 21.7±0.2°, 22.9±0.2° and 27.4±0.2°.

20. The crystalline form according to claim 19, wherein the crystalline form is selected from the group consisting of:

a crystalline form II of compound A monohydrate:

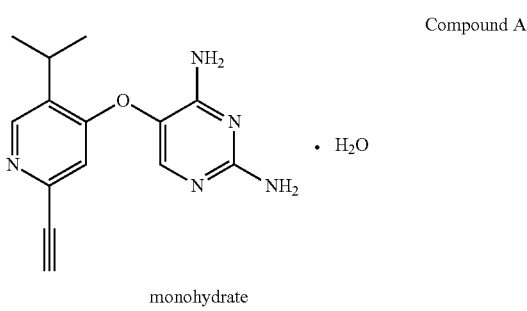 [SMILES: C#Cc1cc(Oc2cnc(N)nc2N)c(C(C)C)cn1 ; O]

monohydrate wherein the crystalline form II has an XRPD pattern comprising characteristic peaks at diffraction angles (2θ) of about 9.6±0.2°, 13.0±0.2°, 19.5±0.2°, 19.9±0.2° and 22.7±0.2°;

a crystalline form III of compound A hemihydrate:

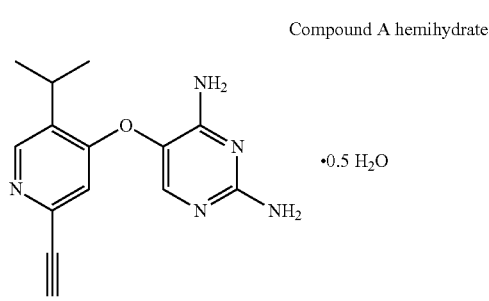 [SMILES: C#Cc1cc(Oc2cnc(N)nc2N)c(C(C)C)cn1 ; "·0.5 H2O"]

wherein the crystalline form III has an XRPD pattern comprising characteristic peaks at diffraction angles (2θ) of about 10.8±0.2°, 19.3±0.2°, 20.5±0.2°, 21.7±0.2° and 26.9±0.2°;

a crystalline form IV of compound A sesquihydrate:

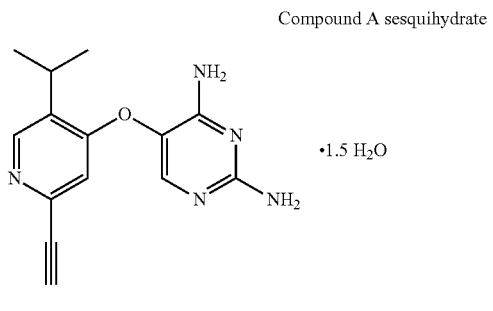 [SMILES: C#Cc1cc(Oc2cnc(N)nc2N)c(C(C)C)cn1 ; "·1.5 H2O"]

wherein the crystalline form IV has an XRPD pattern comprising characteristic peaks at diffraction angles (2θ) of about 12.3±0.2°, 12.6±0.2°, 17.2±0.2°, 20.0±0.2°, 20.6±0.2°, 21.3±0.2°, 23.8±0.2°, 24.1±0.2°, 25.0±0.2° and 27.9±0.2°;

a crystalline form V of compound A monohydrate:

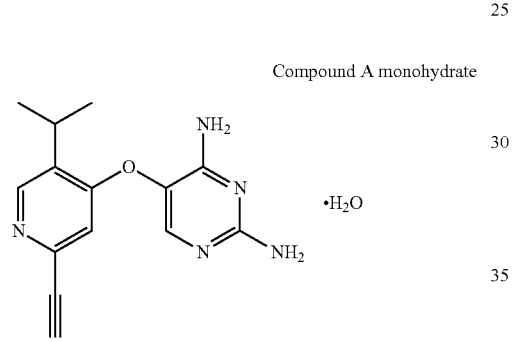

wherein the crystalline form V has an XRPD pattern comprising characteristic peaks at diffraction angles (2θ) of about 8.7±0.2°, 9.4±0.2°, 11.9±0.2°, 14.1±0.2°, 15.8±0.2°, 16.8±0.2°, 18.9±0.2°, 19.9±0.2°, 20.6±0.2°, 21.0±0.2°, 22.5±0.2° and 29.6±0.2°;

a crystalline form VI of compound A monohydrate:

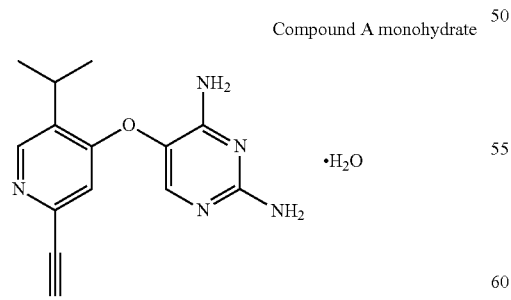

wherein the crystalline form VI has an XRPD pattern comprising characteristic peaks at diffraction angles (2θ) of about 8.7±0.2°, 10.4±0.2°, 12.1±0.2°, 15.4±0.2°, 16.6±0.2°, 19.5±0.2°, 20.7±0.2°, 21.2±0.2°, 22.8±0.2° and 27.3±0.2°;

a crystalline form VII of compound A sesquihydrate:

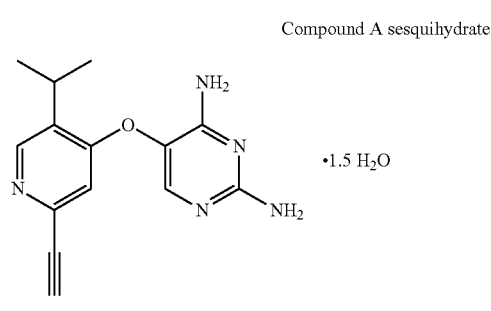

wherein the crystalline form VII has an XRPD pattern comprising characteristic peaks at diffraction angles (2θ) of about 13.1±0.2°, 16.9±0.2°, 19.9±0.2°, 20.2±0.2°, 24.9±0.2° and 28.8±0.2°; or a crystalline form VIII of compound A hemihydrate:

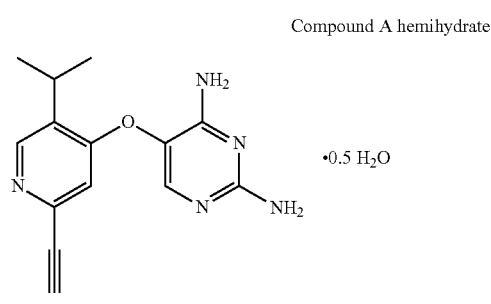 [SMILES: C#Cc1cc(Oc2cnc(N)nc2N)c(C(C)C)cn1 ; "·0.5 H2O"]

wherein the crystalline form VIII has an XRPD pattern comprising characteristic peaks at diffraction angles (2θ) of about 10.3±0.2°, 13.0±0.2°, 16.8±0.2°, 19.1±0.2°, 19.4±0.2°, 21.1±0.2°, 21.7±0.2°, 22.9±0.2°, 25.8±0.2° and 27.4±0.2°.

21. The crystalline form according to claim 19, wherein the crystalline form is selected from the group consisting of:

a crystalline form II of compound A monohydrate:

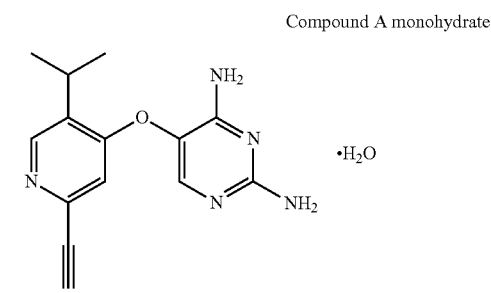

wherein the crystalline form II has an XRPD pattern comprising characteristic peaks at diffraction angles (2θ) of about 9.6±0.2°, 10.9±0.2°, 13.0±0.2°, 14.9±0.2°, 15.8±0.2°, 16.8±0.2°, 19.5±0.2°, 19.9±0.2°, 22.7±0.2°, 23.7±0.2°, 25.2±0.2°, 26.0±0.2°, 28.5±0.2°, 29.0±0.2°, 30.0±0.2° and 32.5±0.2°;

a crystalline form III of compound A hemihydrate:

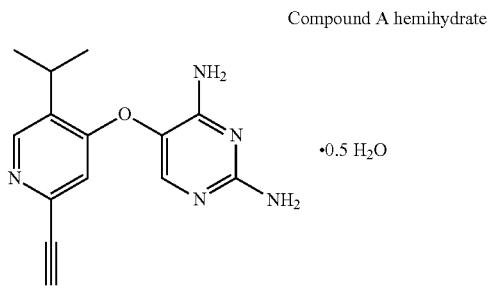 [SMILES: C#Cc1cc(Oc2cnc(N)nc2N)c(C(C)C)cn1 ; "·0.5 H2O"]
Compound A hemihydrate
•0.5 H₂O wherein the crystalline form III has an XRPD pattern comprising characteristic peaks at diffraction angles (2θ) of about 10.8±0.2°, 13.0±0.2°, 15.0±0.2°, 15.4±0.2°, 16.5±0.2°, 17.3±0.2°, 19.3±0.2°, 19.9±0.2°, 20.5±0.2°, 21.7±0.2°, 23.3±0.2°, 25.1±0.2°, 26.5±0.2°, 26.9±0.2°, 28.7±0.2° and 32.2±0.2°;

a crystalline form IV of compound A sesquihydrate:

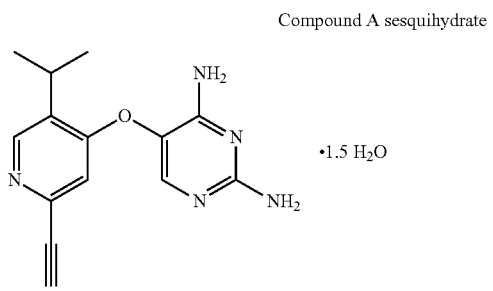 [SMILES: C#Cc1cc(Oc2cnc(N)nc2N)c(C(C)C)cn1 ; "·1.5 H2O"]
Compound A sesquihydrate
•1.5 H₂O wherein the crystalline form IV has an XRPD pattern comprising characteristic peaks at diffraction angles (2θ) of about 12.3±0.2°, 12.6±0.2°, 14.3±0.2°, 17.2±0.2°, 20.0±0.2°, 20.6±0.2°, 21.3±0.2°, 23.2±0.2°, 23.8±0.2°, 24.1±0.2°, 25.0±0.2°, 25.7±0.2°, 27.9±0.2°, 31.2±0.2° and 31.7±0.2°;

a crystalline form V of compound A monohydrate:

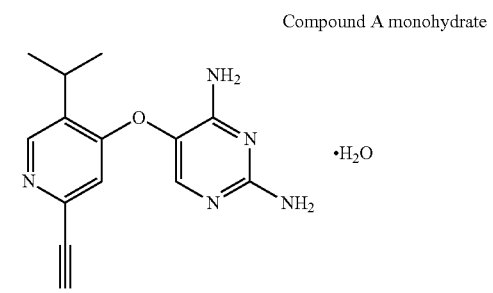 [SMILES: C#Cc1cc(Oc2cnc(N)nc2N)c(C(C)C)cn1 ; O]
Compound A monohydrate
•H₂O wherein the crystalline form V has an XRPD pattern comprising characteristic peaks at diffraction angles (2θ) of about 8.7±0.2°, 9.4±0.2°, 11.6±0.2°, 11.9±0.2°, 12.4±0.2°, 14.1±0.2°, 14.5±0.2°, 15.8±0.2°, 16.2±0.2°, 16.8±0.2°, 17.6±0.2°, 18.2±0.2°, 18.9±0.2°, 19.9±0.2°, 20.6±0.2°, 21.0±0.2°, 22.5±0.2°, 23.0±0.2°, 23.6±0.2°, 24.4±0.2°, 25.2±0.2°, 27.0±0.2° and 29.6±0.2°;

a crystalline form VI of compound A monohydrate:

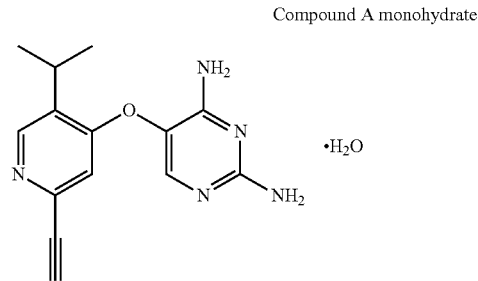 [SMILES: C#Cc1cc(Oc2cnc(N)nc2N)c(C(C)C)cn1 ; O]
Compound A monohydrate
•H₂O wherein the crystalline form VI has an XRPD pattern comprising characteristic peaks at diffraction angles (2θ) of about 8.7±0.2°, 10.4±0.2°, 12.1±0.2°, 13.4±0.2°, 14.7±0.2°, 15.4±0.2°, 16.6±0.2°, 17.4±0.2°, 19.5±0.2°, 20.7±0.2°, 21.2±0.2°, 22.1±0.2°, 22.8±0.2°, 23.6±0.2°, 26.0±0.2°, 27.3±0.2°, 28.0±0.2° and 30.4±0.2°;

a crystalline form VII of compound A sesquihydrate:

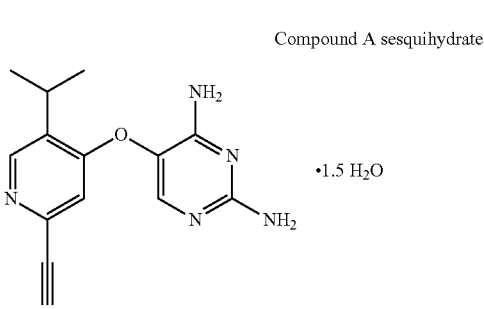
Compound A sesquihydrate
•1.5 H₂O wherein the crystalline form VII has an XRPD pattern comprising characteristic peaks at diffraction angles (2θ) of about 9.4±0.2°, 10.8±0.2°, 13.1±0.2°, 15.4±0.2°, 16.9±0.2°, 18.8±0.2°, 19.9±0.2°, 20.2±0.2°, 22.2±0.2°, 23.2±0.2°, 24.9±0.2°, 26.4±0.2° and 28.8±0.2°; or a crystalline form VIII of compound A hemihydrate:

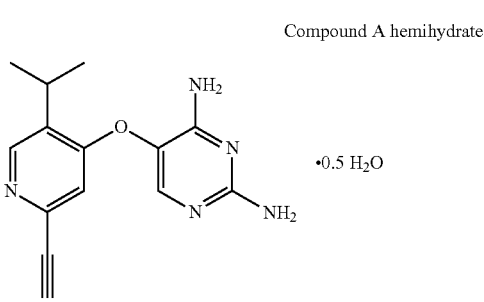 [SMILES: C#Cc1cc(Oc2cnc(N)nc2N)c(C(C)C)cn1 ; "·0.5 H2O"]
Compound A hemihydrate
•0.5 H₂O wherein the crystalline form VIII has an XRPD pattern comprising characteristic peaks at diffraction angles (2θ) of about 8.7±0.2°, 10.3±0.2°, 10.8±0.2°, 13.0±0.2°, 14.1±0.2°, 14.8±0.2°, 16.8±0.2°, 17.5±0.2°, 19.1±0.2°, 19.4±0.2°, 21.1±0.2°, 21.7±0.2°, 22.3±0.2°, 22.9±0.2°, 25.8±0.2°, 27.4±0.2°, 27.8±0.2°, 30.4±0.2° and 31.6±0.2°.

22. A pharmaceutical composition comprising any one of the crystalline forms of claim 19, and one or more pharmaceutically acceptable carriers.

23. A method for the prevention or treatment of a disease mediated by a P2X3 and/or P2X2/3 receptor antagonist, comprising administering to a subject in need thereof any one of the crystalline forms according to claim 19.

24. The method according to claim 23, wherein the disease is selected from the group consisting of a urinary tract disease selected from reduced bladder capacity, frequent micturition, urge incontinence, stress incontinence, bladder hyperreactivity, benign prostatic hypertrophy, prostatitis, detrusor hyperreflexia, nocturia, urinary urgency, pelvic hypersensitivity, urethritis, pelvic pain syndrome, prostatodynia, cystitis, and idiopathic bladder hypersensitivity; a pain disease selected from inflammatory pain, surgical pain, visceral pain, dental pain, premenstrual pain, central pain, pain due to burns, migraine and cluster headaches, nerve injury, neuritis, neuralgia, poisoning, ischemic injury, interstitial cystitis, cancer pain, viral, parasitic or bacterial infection, post-traumatic injury and pain associated with irritable bowel syndrome; a cardiovascular system disease; a respiratory disease selected from chronic obstructive pulmonary disease, asthma and bronchospasm; a gastrointestinal disease selected from irritable bowel syndrome, inflammatory bowel disease, biliary colic, renal colic, and pain associated with gastrointestinal distension.

25. The method according to claim 24, wherein the cardiovascular system disease is hypertension; and the irritable bowel syndrome is diarrhea-dominant irritable bowel syndrome.

* * * * *

UNITED STATES PATENT AND TRADEMARK OFFICE
CERTIFICATE OF CORRECTION

PATENT NO. : 12,365,665 B2  
APPLICATION NO. : 17/607449  
DATED : July 22, 2025  
INVENTOR(S) : Cheng et al.

Page 1 of 1

It is certified that error appears in the above-identified patent and that said Letters Patent is hereby corrected as shown below:

On the Title Page

Please insert, immediately following item (65):  
--(63) Related U.S. Application Data  
National Stage Entry of PCT/CN2020/087687, filed on April 29, 2020.--

Please insert, immediately following item (63):  
--(30) Foreign Application Priority Data  
Apr. 30, 2019 (CN)...................... PCT/CN2019/085207--

Signed and Sealed this  
Twenty-first Day of October, 2025

John A. Squires  
*Director of the United States Patent and Trademark Office*